(12) United States Patent
Carpenter

(10) Patent No.: US 6,602,719 B1
(45) Date of Patent: *Aug. 5, 2003

(54) METHOD AND DEVICE FOR DETECTING ANALYTES IN FLUIDS

(75) Inventor: Charles Carpenter, Scarborough, ME (US)

(73) Assignee: IDEXX Laboratories, Inc., Westbrook, ME (US)

(*) Notice: Subject to any disclaimer, the term of this patent is extended or adjusted under 35 U.S.C. 154(b) by 0 days.

This patent is subject to a terminal disclaimer.

(21) Appl. No.: 09/277,715

(22) Filed: Mar. 26, 1999

(51) Int. Cl.⁷ ............................................. G01N 33/553
(52) U.S. Cl. ...................... 436/518; 436/528; 436/530; 436/541; 435/7.1; 435/7.9; 435/287.1; 435/287.2; 435/287.7; 435/286.5; 435/810; 435/970; 422/68.1; 422/70; 422/99
(58) Field of Search ................. 435/7.1, 7.9, 287.1, 435/287.2, 287.7, 286.5, 810, 970; 436/518, 528, 530, 541; 422/68.1, 70, 99

(56) References Cited

U.S. PATENT DOCUMENTS

| | | | |
|---|---|---|---|
| 3,607,093 A | 9/1971 | Stone | 23/253 |
| 3,791,933 A | 2/1974 | Moyer et al. | 195/127 |
| 3,801,466 A | 4/1974 | Denney | 195/103.5 R |
| 3,802,842 A | 4/1974 | Lange et al. | 23/253 TP |
| 3,811,840 A | 5/1974 | Bauer et al. | 23/253 |
| 3,819,488 A | 6/1974 | Rush et al. | 195/103.5 |
| 3,902,052 A | 8/1975 | Amar et al. | 235/151.35 |
| 3,964,871 A | 6/1976 | Hochstrasser | 23/253 |
| 3,992,158 A | 11/1976 | Przybylowicz et al. | 23/253 |
| 4,042,335 A | 8/1977 | Clement | 23/253 |
| 4,059,405 A | 11/1977 | Sodickson et al. | 23/230 R |
| 4,061,468 A | 12/1977 | Lange et al. | 23/253 |
| 4,125,372 A | 11/1978 | Kawai et al. | 23/230 B |
| 4,160,008 A | 7/1979 | Fenocketti et al. | 422/56 |
| 4,277,561 A | 7/1981 | Monget et al. | 435/14 |
| 4,288,228 A | 9/1981 | Oberhardt | 23/230 R |
| 4,303,408 A | 12/1981 | Kim et al. | 23/230 |

(List continued on next page.)

FOREIGN PATENT DOCUMENTS

| | | |
|---|---|---|
| WO | WO 89/06138 | 7/1989 |
| WO | 91/18110 | 11/1991 |
| WO | WO 93/03176 | 2/1993 |
| WO | WO 94/20533 | 9/1994 |
| WO | WO 94/23300 | 10/1994 |

OTHER PUBLICATIONS

Patton, W.F.; *Biologist's Perspective on Analytical Imaging Systems as Applied to Protein Gel Electrophoresis*; Journal of Chromatography A, NL, Elsevier Science; vol. 698; No. 1; Apr., 28, 1995; pp. 55–87; XP004022952; ISSN: 0021–9673; abstract.

Primary Examiner—Christopher L. Chin
Assistant Examiner—Pensee T. Do
(74) Attorney, Agent, or Firm—Foley & Lardner

(57) ABSTRACT

A disposable, dry chemistry analytical system is disclosed which is broadly useful for the detection of a variety of analytes present in biological fluids such as whole blood, serum, plasma, urine and cerebral spinal fluid. The invention discloses the use of the reaction interface that forms between two liquids converging from opposite directions within a bibulous material. The discovery comprises a significant improvement over prior art disposable, analytical reagent systems in that the detectable reactant zone is distinct and separate from the unreacted reagents allowing for the use of reaction indicators exhibiting only minor changes as well as extremely high concentrations of reactants. In addition, staged, multiple reagents can be incorporated. Whole blood can be used as a sample without the need for separate cell separating materials. Finally, the invention is useful for the detection of analytes in a broad variety of materials such as milk, environmental samples, and other samples containing target analytes.

30 Claims, 21 Drawing Sheets

U.S. PATENT DOCUMENTS

| | | | | |
|---|---|---|---|---|
| 4,588,696 | A | 5/1986 | Eskelson | 436/130 |
| 4,594,327 | A | 6/1986 | Zuk | 436/514 |
| 4,627,918 | A | 12/1986 | Saxena | 210/656 |
| 4,637,978 | A | 1/1987 | Dappen | 435/11 |
| 4,654,127 | A | 3/1987 | Baker et al. | 204/1 T |
| 4,774,192 | A | 9/1988 | Terminiello et al. | 436/530 |
| 4,790,979 | A | 12/1988 | Terminiello et al. | 422/56 |
| 4,800,162 | A | 1/1989 | Matson | 435/280 |
| 4,812,400 | A | 3/1989 | Steinman | 435/21 |
| 4,839,297 | A | 6/1989 | Freitag et al. | 436/170 |
| 4,914,020 | A | 4/1990 | Arai et al. | 435/4 |
| 4,935,346 | A | 6/1990 | Phillips et al. | 435/14 |
| 4,940,782 | A | 7/1990 | Rup et al. | 530/387 |
| 4,943,522 | A | 7/1990 | Eisinger et al. | 435/7 |
| 4,962,021 | A | 10/1990 | Meserol et al. | 435/7 |
| 4,973,465 | A | 11/1990 | Baurain et al. | 424/406 |
| 5,061,381 | A | 10/1991 | Burd | 210/789 |
| 5,082,626 | A | 1/1992 | Grage, Jr. | 422/56 |
| 5,091,188 | A | 2/1992 | Haynes | 434/450 |
| 5,096,809 | A | 3/1992 | Chen et al. | 435/7.9 |
| 5,114,350 | A | 5/1992 | Hewett | 435/288 |
| 5,122,284 | A | 6/1992 | Braynin et al. | 210/782 |
| 5,130,258 | A | 7/1992 | Makino et al. | 436/169 |
| 5,135,716 | A | 8/1992 | Thakore | 422/56 |
| 5,147,606 | A | 9/1992 | Charlton et al. | 422/56 |
| 5,186,844 | A | 2/1993 | Burd et al. | 210/782 |
| 5,187,100 | A | 2/1993 | Matzinger et al. | 436/16 |
| 5,212,060 | A | 5/1993 | Maddox | 435/7.1 |
| 5,242,606 | A | 9/1993 | Braynin et al. | 210/787 |
| 5,252,293 | A | 10/1993 | Drbal et al. | 422/101 |
| 5,304,348 | A | 4/1994 | Burd et al. | 422/72 |
| 5,341,215 | A | 8/1994 | Seher | 356/445 |
| 5,342,924 | A | 8/1994 | Chang | 530/387.9 |
| 5,389,524 | A | 2/1995 | Larson et al. | 435/29 |
| 5,397,710 | A | 3/1995 | Steinman | 436/79 |
| 5,403,415 | A | 4/1995 | Schembri | 156/73.1 |
| 5,408,535 | A | 4/1995 | Howard, III et al. | 382/1 |
| 5,409,665 | A | 4/1995 | Burd | 422/64 |
| 5,413,732 | A | 5/1995 | Buhl et al. | 252/182.11 |
| 5,422,258 | A | 6/1995 | Chang | 435/172.2 |
| 5,457,030 | A | 10/1995 | Badal et al. | 435/34 |
| 5,472,603 | A | 12/1995 | Schembri | 210/380.1 |
| 5,478,750 | A | 12/1995 | Bernstein et al. | 436/164 |
| 5,518,930 | A | 5/1996 | Burd | 436/45 |
| 5,543,144 | A | 8/1996 | Chang | 424/133.1 |
| 5,563,042 | A | 10/1996 | Phillips et al. | 435/14 |
| 5,591,643 | A | 1/1997 | Schembri | 436/45 |
| 5,599,411 | A | 2/1997 | Schembri | 156/73.1 |
| 5,601,991 | A | 2/1997 | Oberhardt | 435/7.91 |
| 5,629,415 | A | 5/1997 | Hollis et al. | 536/23.53 |
| 5,653,980 | A | 8/1997 | Hellman | 424/184.1 |
| 5,693,233 | A | 12/1997 | Schembri | 210/787 |
| 5,716,852 | A | 2/1998 | Yager et al. | 436/172 |
| 5,726,064 | A | 3/1998 | Robinson et al. | 436/514 |
| 5,776,719 | A | 7/1998 | Douglas et al. | 435/28 |
| 5,779,867 | A | 7/1998 | Shieh | 204/403 |
| 5,802,842 | A | 9/1998 | Hook et al. | 60/271 |
| 5,824,268 | A * | 10/1998 | Bernstein et al. | |
| 5,856,203 | A | 1/1999 | Robinson et al. | 436/518 |
| 5,948,684 | A | 9/1999 | Weigl et al. | 436/52 |
| 5,998,221 | A | 12/1999 | Malick et al. | 436/514 |
| 6,027,944 | A | 2/2000 | Robinson et al. | 436/518 |
| 6,136,610 | A | 10/2000 | Polito et al. | 436/514 |
| 6,222,619 | B1 | 4/2001 | Herron et al. | 356/39 |
| 6,316,274 | B1 | 11/2001 | Herron et al. | 436/518 |

* cited by examiner

Glucose Assay (Trinder Reagent Dried on Membrane)

Dried reagent streaking at reconstitution 246 mg/dL Glucose, T=0

T=5 Seconds

T=10 Seconds

Glucose Assay (Trinder Reagent Dried on Membrane)

T=20 Seconds

T=30 Seconds

T=2 Minutes

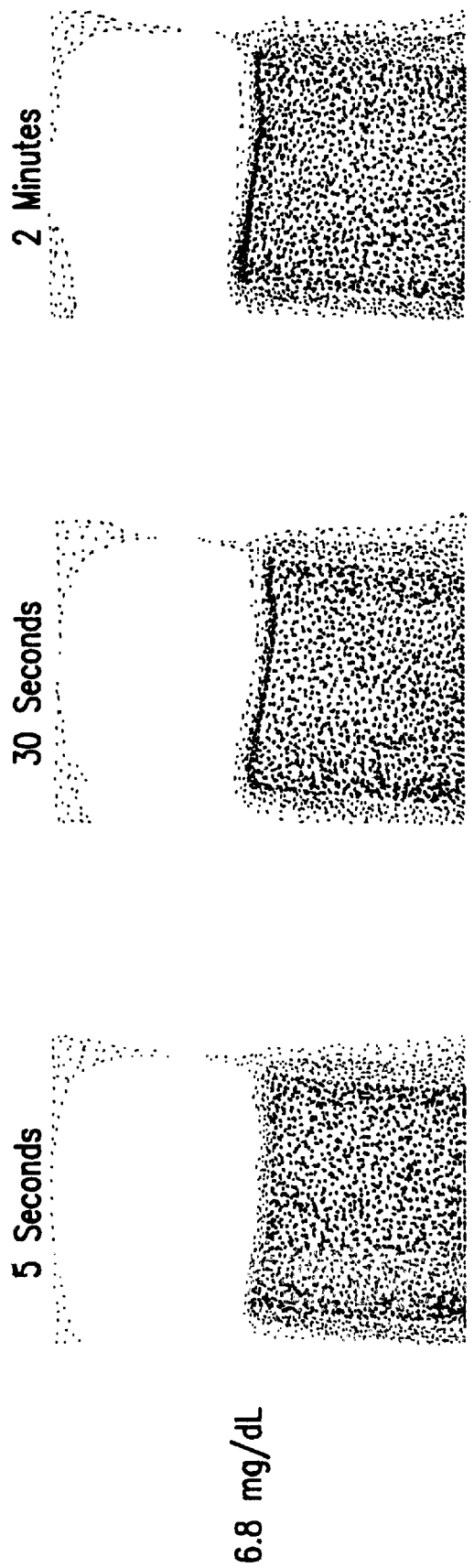

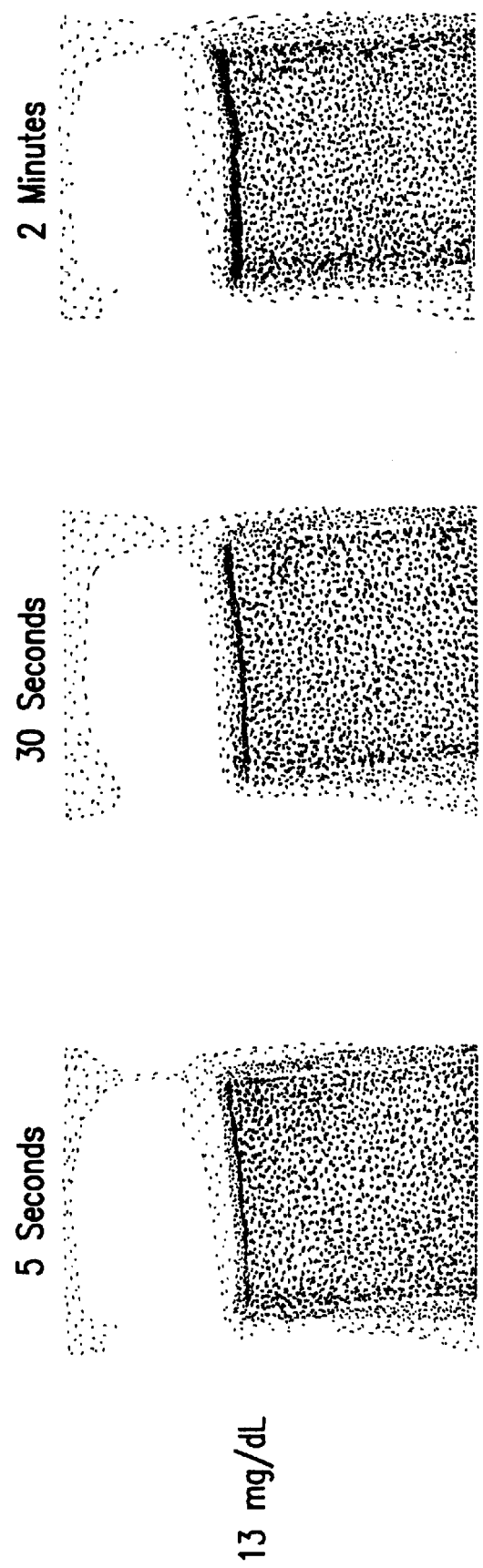

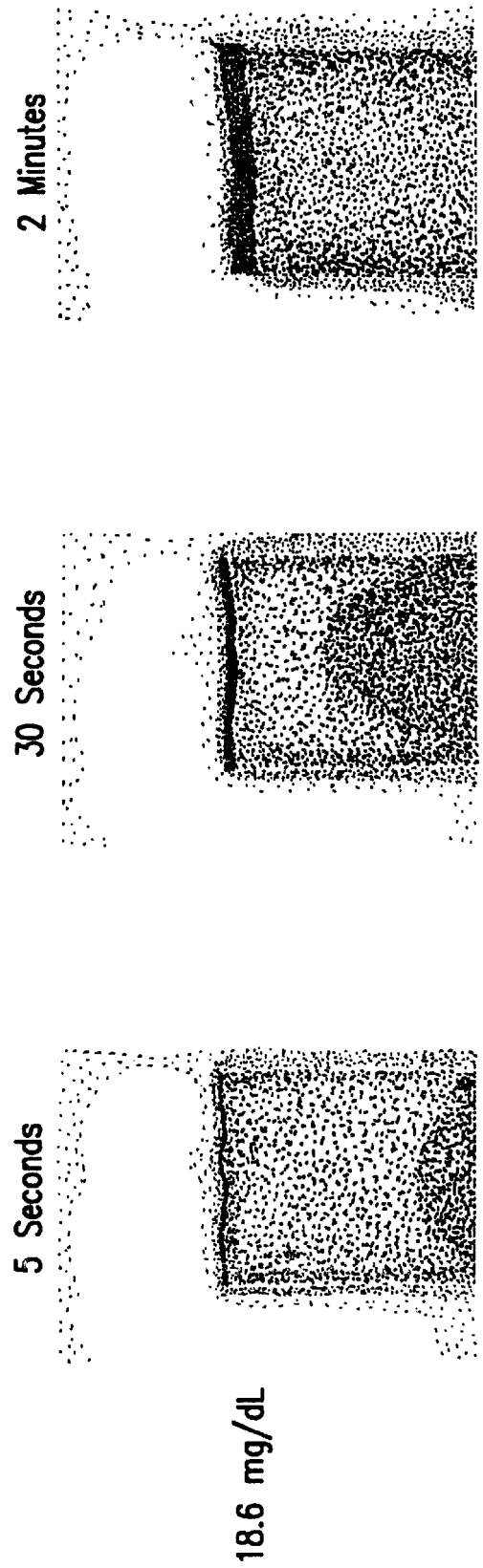

METHOD AND DEVICE FOR DETECTING ANALYTES IN FLUIDS

The present invention relates to test devices and methods for the determination of analytes which may be present in liquids.

BACKGROUND OF THE INVENTION

The quantification of chemical and biological components in aqueous solutions such as whole blood, plasma, serum and urine is important for the timely and correct diagnosis of various diseases, as well as for monitoring the progress of the medical treatment of diseases. In many cases the analytes being measured are present in only tiny amounts and are often mixed with much larger amounts of irrelevant or interfering components. Some components such as red blood cells prevent the analysis of the sample if they are present. Also problematic are the reagents and indicators used to detect and measure the analytes. These reagents are often highly colored and closely resemble the reaction products in terms of their absorbance spectra. In addition, the measurement of analytes often requires multiple, incompatible reagents that must be stored separately and added sequentially. Any of these factors may complicate the detection and quantification of analytes in fluid samples.

These problems and issues have been addressed in a variety of ways. Analytical methods used can be divided into two broad categories of assay formats: liquid chemistry formats and dry chemistry formats. Liquid chemistry systems require that sample and liquid reagents be dispensed into reaction chambers in a timed, sequential order. Samples must often be diluted with special buffers to reduce or eliminate interfering compounds and are then added to reagents designed to react with specific analytes. In some cases, multiple reagents must be premixed immediately before use due to stability problems. In other cases additional reagents may be needed to provide color-producing, readable reactions. The results may be obtained by measuring the absorption of light by the fluid sample. Reactions involving decreases in reaction color or minor differences in color changes may further require separate tubes of reagents to standardize the results or serve as controls.

Dry chemistry systems utilize reagents dried onto absorbent surfaces. Most commercially available products have multiple layers of reactants sandwiched together. Some are arranged vertically and some combine vertical and horizontal arrangements. In all cases, dry chemistry systems using chromogenic reactions rely on measuring light reflected off of either the top or bottom surface of the final reagent pad. The assaying of whole blood presents additional problems since it requires a separate method for separating red blood cells from the sample such as centrifugation or the use of blood separating filter(s) which separate the plasma for analysis. The essence of dry chemistry analysis is to contain a liquid reaction so that colored reaction products can be visualized. This is done with gels and polymers manufactured by, for example, Kodac/Reflotron on fibrous paper-like materials manufactured by, for example, Miles/Ames. In all cases the reaction must be observed among a mixture of sample, diluant, reactants and product which can result in difficulties distinguishing product from non-product. In addition, since all or part of the original reactant is consumed, it can be impossible to reference back to the starting material, such as to establish a reagent baseline. In contrast, the present invention retains all components for further evaluations.

In methods that require precise reaction timing, such as those requiring rapid reactions or measuring a rate of change, it is often difficult to determine the exact start time of the reactions. In most cases the performance of the assay, and therefore the reliability of the results, is dependent on the ability of the test system to evenly deliver a certain amount of liquid (usually blood plasma or serum) to a final reactant material. This material must absorb a known quantity of liquid with extreme accuracy and reproducibility in order for the results to be useful. The precise volume measurements required to obtain accurate results with these types of assays present particular challenges and make them difficult to work with.

Both liquid and dry chemistry systems are limited in the concentrations of reactants that can be used. These concentration limits are often due to the presence of highly colored reactants that absorb or reflect light at wavelengths that interfere with or obscure the detection of reaction product which may absorb or reflect light at similar wavelengths. Various methods have been employed in attempts to solve this problem. Hochstrasser, U.S. Pat. No. 3,964,871, describe a disposable indicator for measuring substances which registers the concentration of a substance in a given biological fluid with indicia which are directly readable in a convenient notation thereby reducing reliance on comparison with a color intensity scale. Kim et al., U.S. Pat. No. 4,303,408, describe elements with interferent-reducing zones which remove interferents prior to the reaction zone. Despite these attempts, only marginal improvements are possible due to the physical limitations which are inherent in the methods.

U.S. Pat. No. 5,716,852, issued to Yager et al., teaches a channel-cell system for detecting the presence and/or measuring the presence of analyte particles in a sample stream comprising a laminar flow channel, two inlets in fluid connection with the laminar flow channel for respectively conducting into the laminar flow channel an indicator stream which may comprise an indicator substance which indicates the presence of said analyte particles by a detectable change in property when contacted with said analyte particles, and the sample stream. The laminar flow channel has a depth sufficiently small to allow laminar flow of streams and a length sufficient to allow particles of the analyte to diffuse into the indicator stream to the substantial exclusion of the larger particles in the sample stream to form a detection area. An outlet conducts the streams out of the laminar flow channel to form a single mixed stream. Yager discloses the formation of a stable reaction interface that forms between two fluids moving through a capillary tube in the same direction. We disclose the invention of a stable interface that forms when two liquids meet and stop in a flow matrix after conveying from opposite directions. The Yager patent is predicated on the principle of liquid laminar flow, which was known in the art. In contrast, the present invention employs bibulous material to physically contain the liquid interface.

U.S. Pat. No. 5,187,100, issued to Matzinger et al., discusses a control solution for use with a porous reagent strip, and comprises a flexible semisolid polymer dispersed in water, such as polyvinyl acetate in distilled water, with appropriate control glucose concentration levels. This solution is useful in mimicking whole blood in conjunction with porous reagent strips to determine compliance of the strips and meters to established measurement and performance criteria.

U.S. Pat. No. 5,147,606, issued to Charlton et al., teaches a diagnostic device that detects blood analytes with a sample volume as low as 2 microliters in the hematocrit range of 0% to 60%, or higher. This is accomplished by employing a housing with various chambers and compartments for processing the blood. A sample application port in the housing is used to introduce blood into a metering chamber. From the metering chamber, the blood flows to a reaction chamber for analyzing blood analytes. Blood entering the metering chamber flows into a fluid capillary which indicates that an adequate amount of blood has been received in the metering chamber. The reaction compartment includes a reagent and a filter, the latter of which is disposed between the metering chamber and the reagent so that the reagent reacts with the filtered blood.

U.S. Pat. No. 4,839,297, issued to Freitag et al., teaches a test apparatus for the analytical determination of a component of a body fluid with a base layer and at least two planar test layers which, in the initial state of the test carrier, before carrying out the determination, are separate from one another but can be brought into contact with one another by external manipulation. A first test layer and a second test layer are arranged on the base layer essentially next to one another but separated in the initial state by a gap, a contact element being provided which consists of a capillary-active material which is so dimensioned that it can bridge the gap and which is so mounted and arranged that, in a first position, it cannot contact at least one of the test layers but, by external pressure, it can be brought into a second position in which it contacts both test layers in such a manner that a liquid exchange between the test layers is possible.

U.S. Pat. No. 4,637,978, issued to Dappen, discloses an assay useful for the determination of an analyte in whole blood. In particular, this assay is useful for the quantitative determination of peroxide-generating analytes, such as glucose or cholesterol, in whole blood. This assay utilizes a multizone element consisting essentially of a support having thereon, in order and in fluid contact, a registration zone and a reagent/spreading zone. The reagent/spreading zone has a void volume and average pore size effective to accommodate whole blood, and contains an interactive composition necessary for the analysis. Such composition is capable of providing, upon interaction with the analyte, a dye which can be spectrophotometrically detected at a wavelength greater than about 600 mm.

U.S. Pat. No. 4,160,008, issued to Fenocketti et al., teaches a test device for determining the presence of a liquid sample constituent. The device comprises a base support member having attached to it an indicator member which produces a detectable response, such as a color change, in the presence of the sample constituent. The indicator member comprises an upper reagent layer, a lower absorbent layer and a substantially sample-impervious barrier layer between the upper and lower layers. The indicator member is attached to the base member along the lower side of the absorbent layer.

U.S. Pat. No. 4,042,335, issued to Clement, discloses a multilayer element for the analysis of liquids such as biochemical and biological liquids. The invention includes a reagent layer including a composition that is interactive in the presence of a predetermined substance to be analyzed (analyte) to provide a diffusible, detectable species, e.g., a dye, can be detected. Preferably between the reagent layer and the registration layer, there can be a radiation-blocking layer, such as an opaque reflecting layer, to enhance detection of the diffusible species within the registration layer. A spreading layer is separated from the registration layer by a reagent layer. In operation, a sample of liquid under analysis is applied to the reagent layer or, if present, to a spreading layer. If the sample contains analyte, a chemical reaction or other interaction within the reagent layer provides a detectable species that diffuses, via any intervening layers such as a radiation-blocking layer, into the registration layer for detection there, such as by radiometric techniques like reflection spectrophotometry.

U.S. Pat. No. 3,942,158, issued to Przybylowicz et al., discloses an integral analytical element capable of use in the analysis of liquids, the element having at least two superposed layers including a spreading layer and a reagent layer, in fluid contact. The spreading layer, which can be an isotropically porous layer, spreads within itself at least a component of a liquid sample applied to the element, or a reaction product of such component, to obtain a uniform concentration of at least one such spread substance at the surface of the spreading layer which faces the reagent layer. The reagent layer, which is desirable uniformly permeable to at least one dissolved or dispersed component of the liquid sample or a reaction product of such a component, can include a matrix in which is distributed a material that can interact with, for example, an analyte or analyte reaction product to produce a detectable change in the element, such as one detectable by measurement of electromagnetic radiation. In a preferred embodiment, the interactive material can chemically react with an analyte or analyte reaction product to produce a color change in the element. In another preferred embodiment, the sample spreading layer can filter out chemically interfering or other undesirable materials and obtain selective spreading of sample components and/or it can provide a reflective background, often useful in obtaining analytical results.

U.S. Pat. No. 3,811,840, issued to Bauer et al., teaches a test device for detecting low concentrations of substances in test fluids which includes an absorbent wick having a substantially flat surface portion enclosed in a fluid impervious sheath having an aperture of predetermined limited area formed therein. The aperture is contiguous to and exposes a predetermined limited area of the flat surface portion of the wick, which is incorporated with a reagent specifically reactable with the substance being detected. In use the device is immersed into the test fluid so that the aperture is submerged and the device is allowed to remain therein while the test fluid contacts the reagent area adjacent to the aperture and migrates into the remainder of the wick. The reagent is immobilized with respect to the liquid.

U.S. Pat. No. 5,802,842, issued to Lange et al., discloses a test strip for the detecting of components in liquids, especially in body fluids. The test strip includes a holder and at least one indicator layer containing detection reagents. One surface of the indicator layer is attached to the holder and the other surface is covered with a fine meshwork.

Note, however, that the analytical devices of the above prior art employ fluid movement in only a single direction. Because no reaction interface is created by a movement of two fluids in opposite directions, the above prior art references cannot be employed to measure the reaction intensity or reaction rate at a reaction interface, as disclosed by the present invention.

The present invention provides a solution to the problems and deficiencies of current systems discussed above. Specifically, the present invention provides a device which contain all reactants necessary for sample preparation and analyte detection and methods of their use. The present invention provides devices and methods which eliminate the extreme precision in volume measurement which is required by some methods. The results of assays conducted with the present invention are read in a generic reading area of the device, and a wide variety and versatility in reagent chemistry and concentrations is offered.

SUMMARY OF THE INVENTION

The present invention provides a device for detecting and quantifying analytes in a fluid sample. The device is a bibulous material having an application site for the fluid sample in a fluid sample zone and a separate application site for a diluent solution in a diluent solution zone. At least one reagent which is capable of being reconstituted may be present in one or more diluent solution zones and fluid sample zones on the bibulous material. The reagent(s), diluent solution, and fluid sample form a detectable product at a localized interface on the bibulous material upon migration of the fluid sample from one direction and the diluent solution from a second, opposite direction. One or more reagents may be contained on the bibulous material in one or more reagent zones. Reagents to be reconstituted by the fluid sample may be contained by the bibulous material at a site which is closer to the application site for the fluid sample than to the application site for the diluent solution. Conversely, reagents which are to be reconstituted by the diluent solution may be contained by the bibulous material at a site which is closer to the application site for the diluent solution than to the application site for the fluid sample. In a preferred embodiment, the bibulous material may be capable of separating red blood cells from whole blood as the fluid sample travels through the bibulous material. In various embodiments the bibulous material may be a HEMASEP L® membrane, a HEMASEP V® membrane, a CYTOSEP® membrane, a SUPOR® membrane, or a nitrocellulose membrane. In a preferred embodiment, the detectable reaction product may reflect light. The concentration of unreacted reagents on the bibulous material may provide a reference value, control, or blank for the assay. In other embodiments, the reagent or reagents may be contained in an absorbent pad placed in contact with the bibulous material. The absorbent pad may be selected from the group consisting of cellulose, glass fiber, polyester, or any absorbent polymer.

The present invention also provides methods for detecting and quantifying analytes in a fluid sample. The methods consist of the steps of providing a bibulous material as described above, contacting the fluid sample to be assayed and a diluent solution with the bibulous material at their respective application sites, allowing the fluid sample and the diluent solution to flow toward one another wherein the diluent solution and/or the fluid sample reconstitutes one or more reagents which may be present in the bibulous material, allowing the fluid sample and the diluent solution to converge to form an interface thereby reacting to form a detectable product, and examining the interface and thereby determining the presence or quantity of the analytes in the fluid sample by evaluating the presence or amount of the detectable product. The reagent may be a plurality of reagents in a plurality of locations on the bibulous material. The fluid sample may be whole blood, blood plasma, blood serum, urine, or any body fluid.

The present invention also provides a method for detecting and quantifying analytes in a fluid sample wherein the reagents are added to either or both of the fluid sample and diluent solution prior to contact with the bibulous material. In this aspect, the method will include providing a bibulous material as described above, and the bibulous material may contain no reagents. The methods includes the step of contacting the fluid sample and diluent solution with the bibulous material at their respective application sites, allowing the fluid sample and diluent solution to converge to form an interface thereby reacting to form a detectable product, and examining the interface to determine the presence or quantity of analyte in the fluid sample by evaluating the presence or quantity of the detectable product.

BRIEF DESCRIPTION OF THE DRAWINGS

FIGS. 5A–5I are photographs showing results over time of three concentrations of calcium assays performed with the present invention;

DETAILED DESCRIPTIONS OF THE INVENTION

Figure 1:
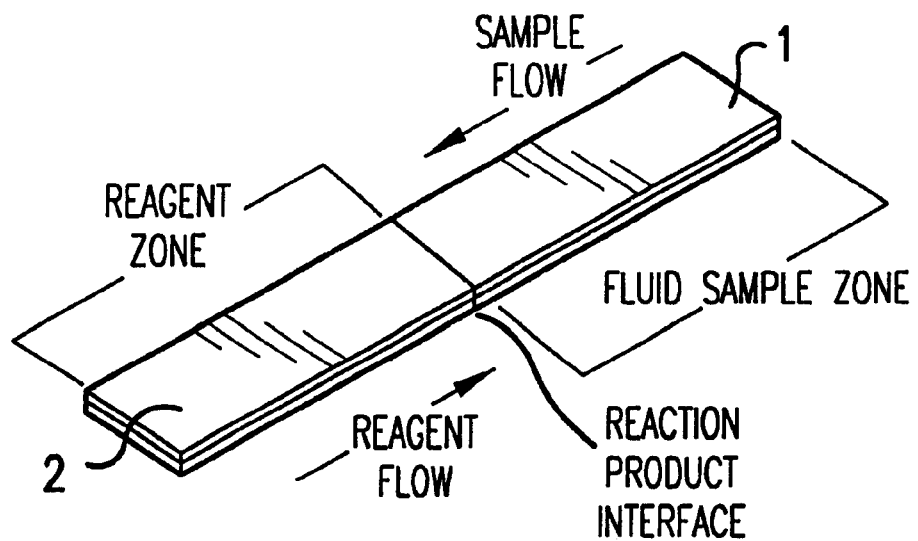
FIG. 1 is an isometric view of the test strip of the present invention showing locations of application sites for fluid sample and diluent solution, direction of diluent solution and fluid sample flow, and reaction product location after completion of the test.

The present invention provides test devices containing dried reagents capable of reacting with analytes which may be present in a fluid sample. The invention may comprise an absorbent strip made of a bibulous material which is capable of absorbing and transporting fluid sample, reagents, and diluent liquids via capillary action. Analytical reagents capable of being dissolved and distributed within the absorbent strip may be dried into the absorbent strip or into reagents pads associated with the absorbent strip. A method for making such dried strips is also provided.

We have observed the unexpected result that two liquids converging from opposite ends of a bibulous material meet at a very sharply defined interface with little mixing of the two opposing solutions over periods of time amounting to several minutes. This allows the creation of a stable reaction interface when the two opposing liquids containing reagents or analytes capable of reacting with each other meet and form a detectable product. The resulting product is localized at the interface for a significant period of time allowing analysis of the reaction rate and the reaction product band intensity without the need to measure starting reagent volumes. Since the reaction product is physically distinct from the reactants, high concentrations of reactants may be used. This allows for the use of large amounts of certain reagents which can counteract endogenous interfering compounds without obscuring results due to closely related absorbency spectra or density of unreacted reagents. The present invention comprises a significant improvement over prior art disposable, analytical reagent systems in that the detectable reactant zone is distinct and separate from the unreacted reagents allowing for the use of reaction indicators exhibiting only minor changes as well as extremely high concentrations of reactants.

Because the reactants are physically distinct from the reaction product, the system contains a built-in sample of both the unreacted fluid sample and the diluent solution which may be used as references for certain types of analytical reactions such as those involving density changes and not spectral changes, or those requiring a starting reagent or reference value.

The devices of the present invention may be made of a bibulous material which supports the capillary flow of liquids from the wet to the dry areas on the device. The bibulous materials of the device may be made of nitrocellulose membranes, cellulose sheets, porous polyethylene, polyethersulfone, or membranes of a variety of other materials. Porous plastics made from a variety of polymers may also be used, such as polyethylene, polystyrene, or polypropylene. These materials are provided as examples and are not intended to be limiting as other appropriate materials may be found. The bibulous material may be any hydrophilic porous material which is capable of absorbing liquids and causing capillary flow. The bibulous material may be adhered to a solid backing such as PVC or polystyrene in order to provide durability in handling. In preferred embodiments for assaying whole blood, the bibulous material may be a material which separates plasma from red blood cells. In these preferred embodiments the bibulous material may be a HEMOSEP V® or HEMOSEP L® membrane (available from Pall-Gelman Inc., Port Washington, N.Y.) or a CYTOSEP® membrane (available from Allstrom Filtration, Mount Holly Springs, Pa.). These materials are provided by way of example and are not intended to be limiting. The person of ordinary skill will realize that a variety of bibulous materials may be successfully utilized in the present invention which have the properties of being able to absorb the sample, support capillary action and thereby facilitate the movement of fluid sample through the material, maintain a defined interface with little mixing of the opposing liquids, and optionally be able to separate plasma from red blood cells.

Regarding hydrophilic absorbent materials, two factors affect usefulness in the present invention. First, the more porous (longer pore size) the less useful as the reaction interface becomes large, diffuse and spreads rapidly. In addition, it appears that the more solids (i.e. less liquid, more volume) the less usable, presumably due to less liquid reaction volume. These two properties hold true until very small pore sizes i.e. 0.45 and 0.22 $\mu$m whereby the reactions are undetectable. It is conceivable that a material of small pore size and low solid may be an excellent material. The best materials known to date are Super 1200 (1.2 $\mu$m) and HEMOSEP L. HEMOSEP L does not have a single pore size, but rather a graded porosity.

The methods and devices of the present invention provide for sample preparation and analysis to be performed in one step on the same device. The device may be a strip having a generally rectangular shape. Alternatively, the bibulous material may also be an array or star-shaped configuration which has the additional advantage of allowing multiple analytes to be analyzed in a single assay. Of course, the person of ordinary skill will realize that the bibulous material may be of any shape advantageous in the particular circumstances.

Figure 2:
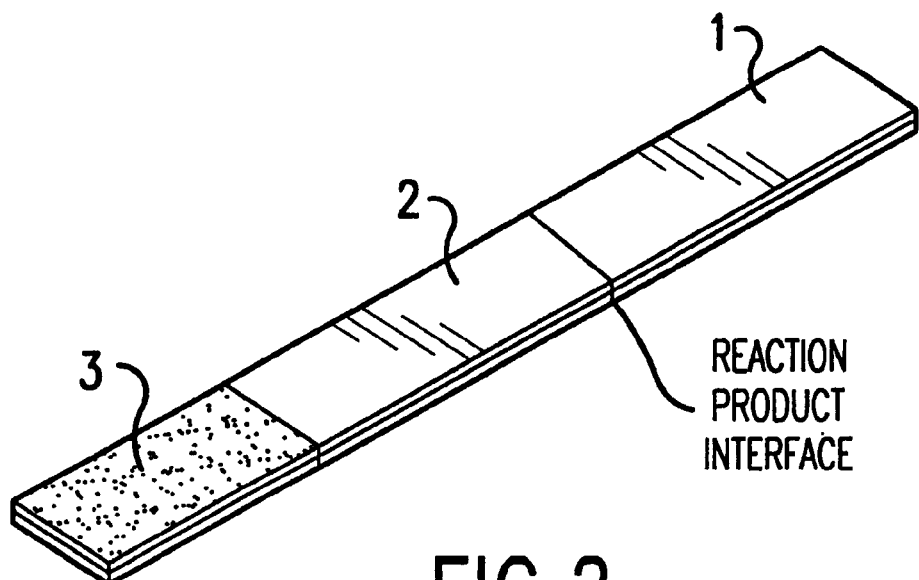
FIG. 2 is an isometric view of another embodiment of the present invention, in which a dried reagent pad containing one or more reagents is attached to one end of the test strip, and the diluent solution application site is located on a portion of the dried reagent pad.

Reagent systems capable of performing chemical evaluation of analytes which are commonly present in biological fluids are known in the art. Of particular interest are those reagent systems utilizing a single component, i.e., where the reaction occurs in a single solution, rather than those requiring more than one timed incubation step. The present invention provides single-component reagent systems composed of several different chemical reagents where the reagents are dried in spatially separated zones on the strips. As shown in FIGS. 1 and 2, dried reagent strips of the present invention may be used by applying a diluent solution ("diluent solution" is defined as any liquid capable of dissolving a reagent. Any reagents which are added to the diluent solution or reconstituted by the diluent solution, are meant to be included in the definition as part of the diluent solution) to one end of the strip and a fluid sample ("fluid sample" is defined as any fluid containing an analyte to be assayed for. Any reagents which are added to the fluid sample, or reconstituted by the fluid sample, are meant to be included in the definition as part of the fluid sample.) to be assayed to the other end. Referring to FIG. 1, the fluid sample may be applied to the fluid sample application site 1 in the fluid sample zone ("fluid sample zone" is defined as any area on the bibulous material which is closer to the fluid sample application site than to the diluent solution application site) and the diluent solution may be applied to the diluent solution application site 2 ("diluent solution zone" is defined as any area on the bibulous material which is closer to the diluent solution application site than to the fluid sample application site). As the two liquids move toward each other through the strips the sample may separate into components. For example, when cell separating strips are used, the fluid sample may separate into plasma and red blood cells. The fluid sample may also reconstitute one or more reagents as it moves through the bibulous material, thereby pre-treating the sample before the final reactions occur. The diluent solution simultaneously travels from the opposite end of the strip dissolving in sequence one or more dried reagents which may be present in the strip. When the fluid sample and the diluent solution containing dissolved reagents meet, a reaction interface forms between the conveying liquids. The reaction products occupy a very narrow band at the interface and are measured for rate and intensity of formation. In a preferred embodiment, the reaction products will be measured using reflected light. However, the person of ordinary skill will realize that other means of measuring the reaction products may also be utilized, such as through the use of conduction, fluorescence or transmission or other methods known in the art which provide a detectable signal related to the presence of a reaction product. The resulting reactant band is stable over several minutes, with little product diffusion into the surrounding area and allows adequate time for the determination of rate and intensity of color development. FIG. 2 illustrates another embodiment of the invention where the one or more reagents which may be present on the bibulous material may be present in the form of a dried reagent pad 3. In this embodiment, the diluent solution application site 2 is located on a portion of the dried reagent pad 3.

Figure 3:
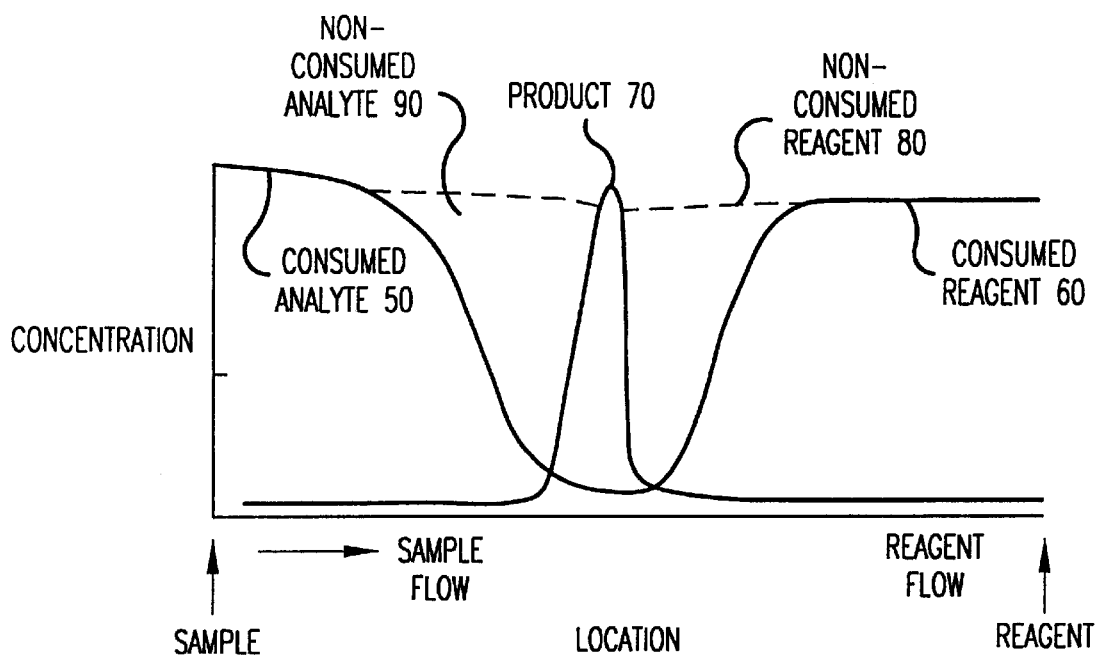
FIG. 3 is a schematic representation of the concentrations of analyte, reagent, and reaction product at locations along the bibulous material and illustrates that at the interface, the concentration of unreacted analyte and reagents falls sharply as they react and form reaction product, and that the concentration of reaction product correspondingly rises sharply at the interface.
Figure 4A:
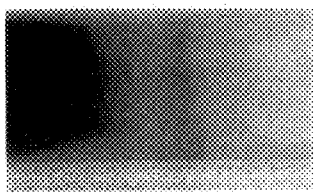
FIGS. 4A–4F are photographs showing results over time of a glucose assay performed with the present invention.
Figure 4B:
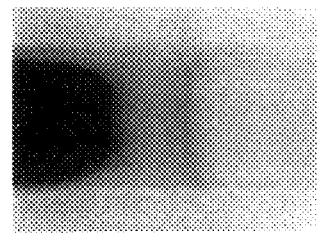
Figure 4C:
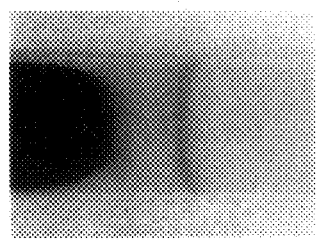
Figure 4D:
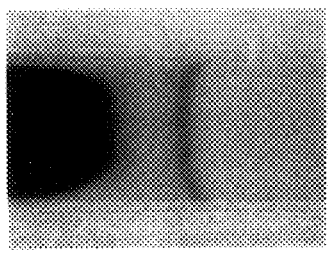
Figure 4E:
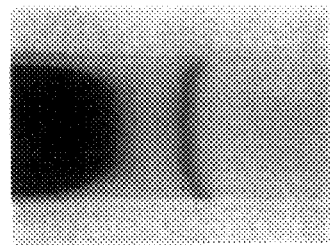
Figure 4F:
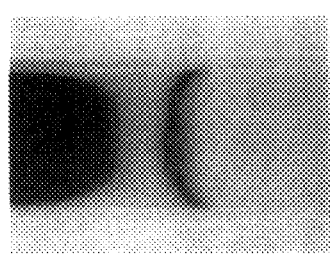
Figure 6:
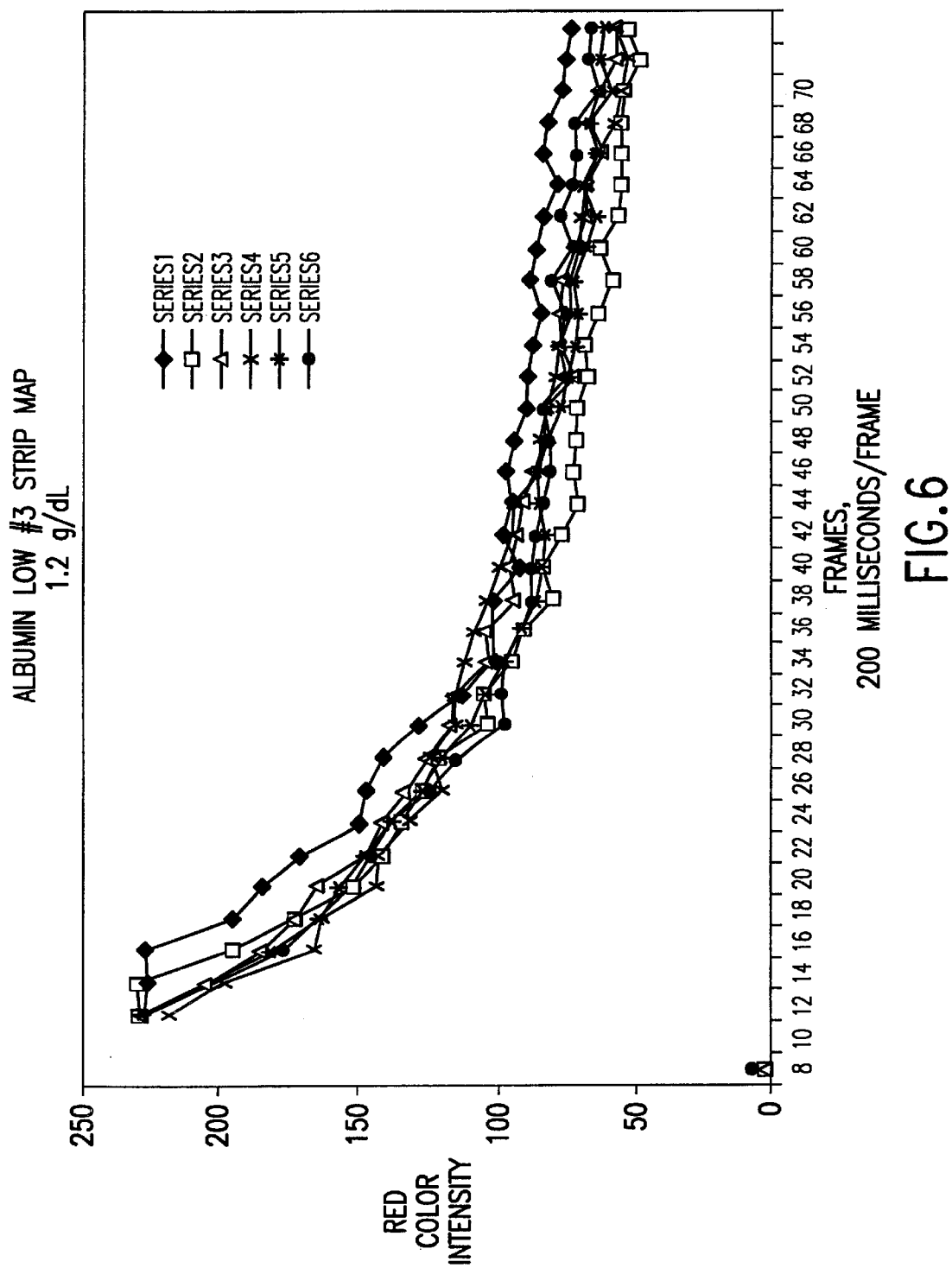
FIG. 6 is a graph of color intensity versus time for six independently read reflective values of a reaction interface from a sample having an albumin concentration of 1.2 g/dl based on an assay run with the present invention.

FIG. 3 is a graphical illustration showing hypothetical relative concentrations of analyte to be assayed, reaction product, and reactant at locations along the bibulous material. The relative concentrations illustrated may be typical of those found on the bibulous material during an assay. FIG. 3 is illustrative of four types assays which may occur on the bibulous material. Line 70 represents product formed. Lines 50 and 60 signify "consumed analyte" and "consumed reagent", respectively, and may illustrate a reaction where the reagent or the analyte is consumed, such as a dye-binding assay where dye is bound to an analyte and both dye and analyte are "consumed" in the complex when the reaction occurs. At the reaction interface, concentrations of unconsumed analyte and unconsumed reagent fall sharply as the concentration of reaction product rises sharply. In other types of reactions, reagent is not consumed in the reaction. For example, in enzymatic assays the enzyme is not consumed but simply converts an analyte (or substrate) to a detectable product. In this case the non-consumed reagent is represented by line 80 and the consumed analyte by line 50. In another type of assay, reagent may be consumed and analyte not consumed such as for a serum enzyme (represented by line 90). There are thus four types of assays which may occur and which are illustrated by FIG. 3: those where analyte is consumed and reagent not consumed, those where analyte is not consumed and reagent is consumed, and those where analyte and reagent are both consumed or not consumed.

Because the reaction interface remains spatially distinct from the fluid sample and reagent solution on the bibulous material, the device incorporates a built-in methodology for determining both reagent and fluid sample concentrations and dilutions.

The device also provides for the internal calculation of reference values which take into account the extent of dilution of reagents in the diluent solution and in the fluid sample (i.e., reflecting the extent to which the dried reagents which may be present have dissolved in the diluent solution or the fluid sample), and for the measurement of background signal, all of which may be useful in certain types of analytical chemistry formats. For example, certain fluid samples may contain material that reflects light at a wavelength at or close to that of the reaction product and this signal must therefore be subtracted from the final reaction product color intensity. In other formats, where results are directly related to reagent concentration, for example in rate reactions where the analytes are in excess, a simultaneous measurement of both starting reagent concentration and product concentration by reflected light intensity at different wavelengths allows adjustment of the resulting analyte concentration values based on variability in the extent of reagent dissolution.

Clinical chemistry assays, whether they are liquid or solid based can be read by kinetic analysis (rate of product formation) or end-point analysis (amount of production at a given time). The present invention offers the only way to measure rate from a true time zone point since one can visualize and time the start of the reaction within milliseconds. This allows one to measure rates within the first few seconds of the assay, which is unique and useful. In addition, a third (i.e. interface band width) can be measured which can correlate with analyte concentration.

In various embodiments, a non-interfering component may be dried onto the fluid sample side of the bibulous material and be assayed at several points along the bibulous material as it is dissolved in the advancing sample fluid front to determine the presence of the sample at the interface. For example, a dye with an absorption spectra distinct from the product may be dried at the fluid sample side of the pad. Measurement of that dye at the fluid sample side of the reaction interface may be performed to determine the presence of fluid sample at the reaction site.

The following is an exemplary, non-comprehensive list of the analytes that can be identified with the present invention: alanine amino transferase (ALT) (enzyme substrate), albumin (dye binding), alkaline phosphatase (enzyme substrate), ammonia (enzymatic), amylase (enzyme substrate), aspartate amino transferase (AST) (enzyme substrate), total bilirubin (dye binding), calcium (dye binding), cholesterol (total) (enzymatic), creatine kinase (CK) (enzyme substrate), creatinine (dye binding), 2-glutamyl transferase (GGT) (enzyme substrate), glucose (enzymatic), lactate dehydrogenase (enzyme substrate), lipase (enzyme substrate), magnesium (dye binding), phosphorus (dye binding), protein (total) (dye binding), triglyceride (enzymatic), urea nitrogen (BUN) (enzymatic), and uric acid (enzymatic). The above referenced reaction types, enzyme substrate, dye bindings and enzymatic, can result in a chronoperic and/or ultraviolet reaction to identify the above listed analytes.

The following examples illustrate the use of the present invention to detect and quantify particular components in a fluid sample. These examples are provided for illustration, and are not intended to be limiting. The person of skill will realize that the principles and techniques illustrated may be applied to detect a variety of analytes in a variety of fluid samples.

EXAMPLE 1

This example illustrates how a device of the present invention was used to determine the presence and concentration (246 mg/dl) of glucose in a sample of whole blood.

A HEMOSEP L® membrane was affixed to an adhesive plastic backing and cut into 4 mm×25 mm strips. Trinder reagent (15 µl) (Sigma Chemical Co., St. Louis, Mo.) containing glucose oxidase (15,000 u/L), 4-aminoantypyrine (0.5 mM), p-hydroxybenzene sulfonate (20 mM) and peroxidase (10,000 u/L) at pH approximately 7.0 was dried onto one end of each test strip, comprising about one-half of the total strip area. This was accomplished by simultaneously dispensing 10 µl of water to one end of the strip (the fluid sample side) and 10 µl of Trinder reagent (at 5× concentration) to the other end of the strip (the diluent solution side). The strip was then air dried for 1 hour at room temperature.

After drying, 15 µl of water was added to the outer end of the diluent solution side of the strip at the diluent solution application site and 15 µl of whole blood was added simultaneously to the outer end of the fluid sample side of the strip at the fluid sample application site. The two liquids flowed towards each other, eventually yielding four distinct bands on the strip: a red blood cell band, a plasma band, a red/brown quinoneimine dye reaction product band (the reaction interface), and a band of unreacted Trinder reagent. As shown in FIGS. 4A–4F, the quinoneimine dye colored product interface band continued to develop over several minutes, with its rate of development and final color intensity being proportional to the starting concentration of glucose in the sample.

EXAMPLE 2

This example illustrates how the present invention was applied to detect and quantify calcium in fetal calf serum.

Three polyethersulfone membranes were prepared as described in Example 1 and washed with 50 µl of water at pH 2.0. An example of a suitable polyethersulfone membrane for use in the present invention is a SUPOR® membrane (available from Pall-Gelman, Inc., Port Washington, N.Y.). The person of ordinary skill will realize that other porous membranes with similar characteristics may also be applied to the present invention. Fifteen microliters of fetal calf serum containing 6.8, 13 and 18.6 mg/dl of calcium was added to the fluid sample side of each strip at the fluid sample application site while simultaneously adding 15 µl of acidified Arsenazo III red/purple dye solution to the diluent solution side of the strip at the diluent solution application site. In each case, the two liquids flowed towards each other and upon meeting formed a discrete interface. The blue reaction product, calcium-arsenazo III, developed at the interface. As shown in FIGS. 5A–5I, both the time for color development and final intensity of blue color were proportional to the starting concentration of calcium in the fluid samples.

EXAMPLE 3

In this example, 1.2 g/dl and 1.9 g/dl concentrations of albumin in fetal calf serum were tested with the present invention using bromocresol green dye after adjustment to pH 5.5.

Figure 7:
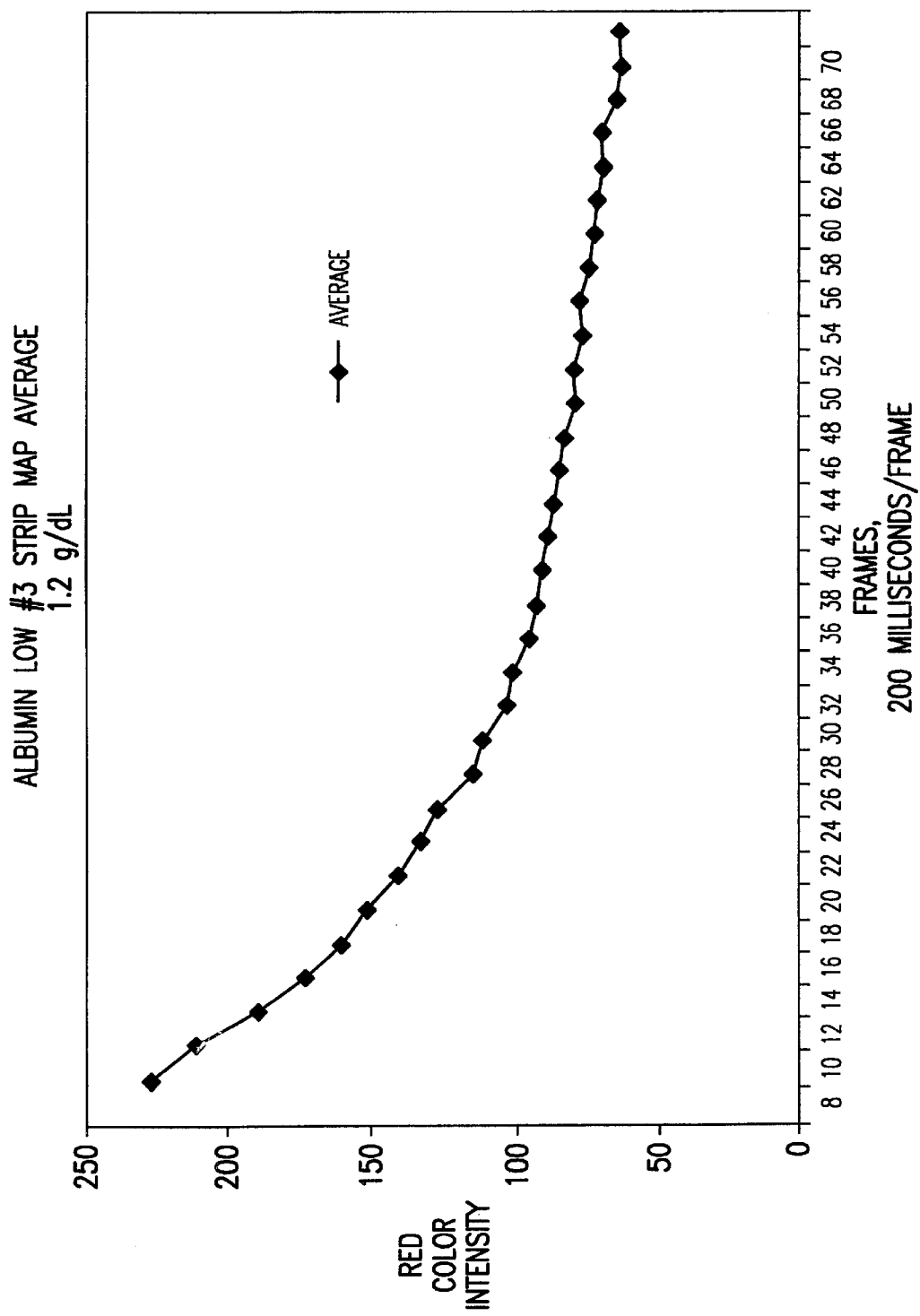
FIG. 7 is a numerical tabulation of color intensity versus time for six independently read reflective values of a reaction interface, and the average value and slope of sample having an albumin concentration of 1.2 g/dl based on an assay run with the present invention.
Figure 8:
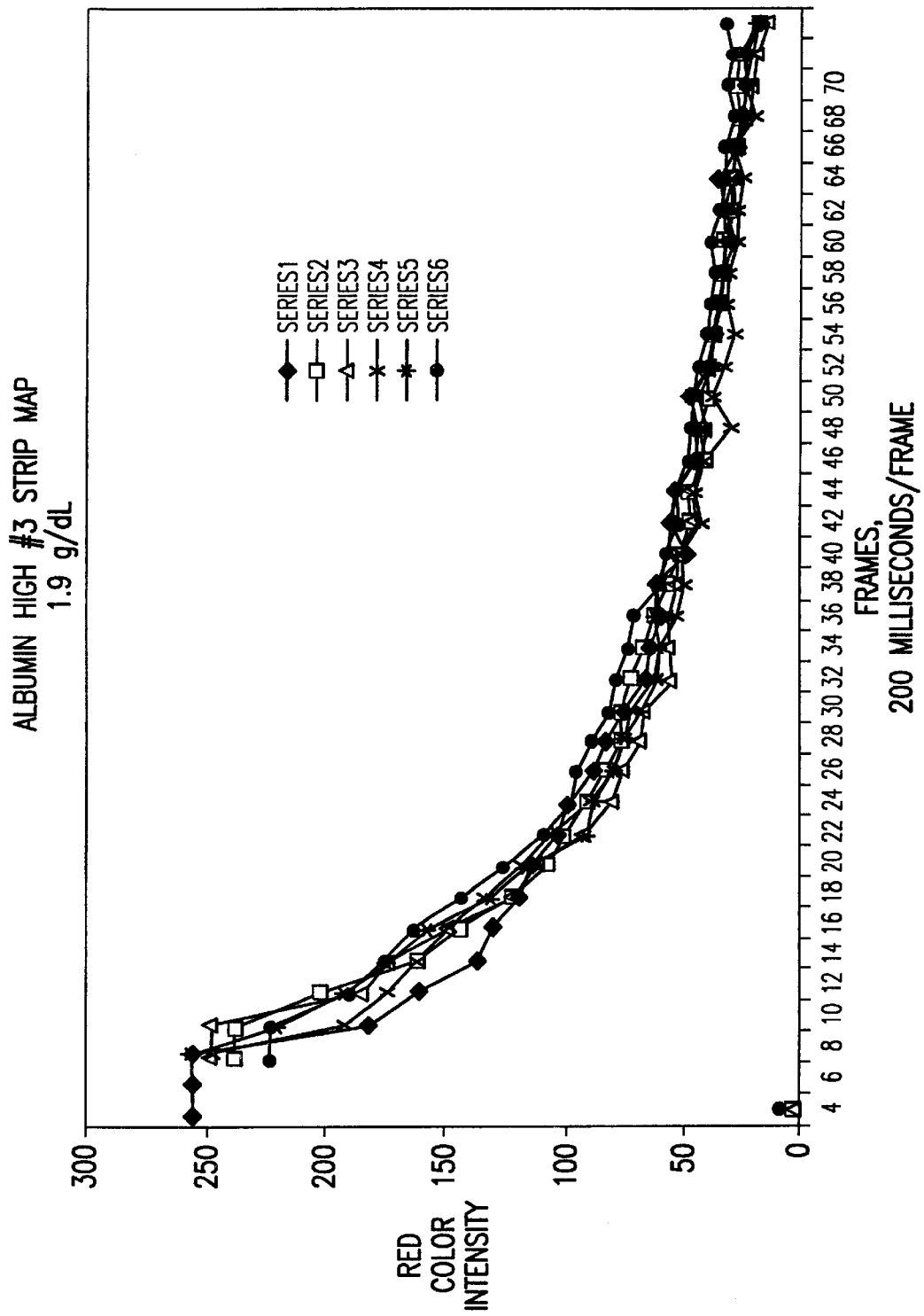
FIG. 8 is a graph of color intensity versus time for six independently read reflective values of a reaction interface from a sample having an albumin concentration of 1.9 g/dl based on an assay run with the present invention.
Figure 9:
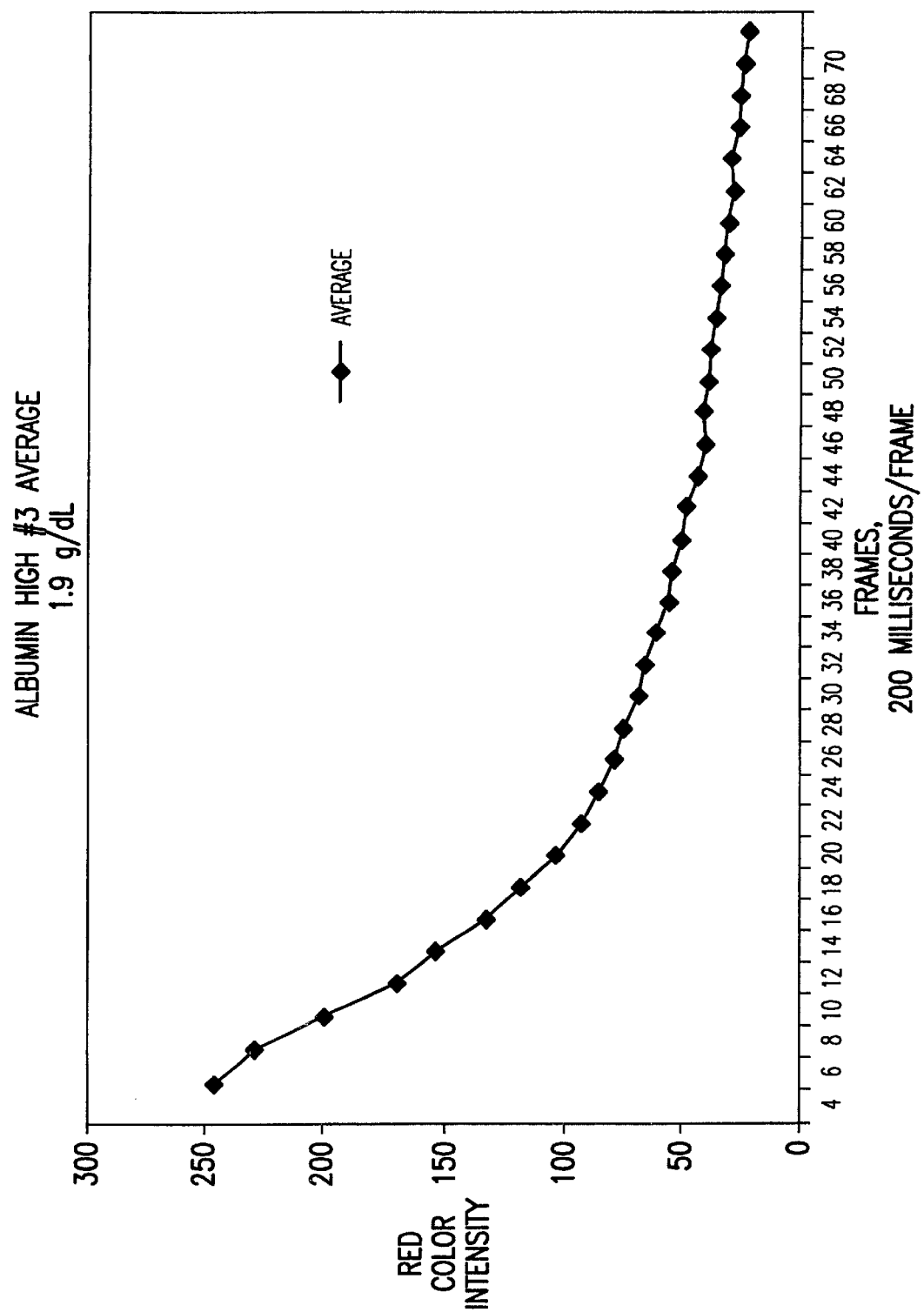
FIG. 9 is a numerical tabulation of color intensity versus time for six independently read reflective values of a reaction interface, and the average value and slope of a sample having an albumin concentration of 1.9 g/dl based on an assay run with the present invention.
Figure 10:
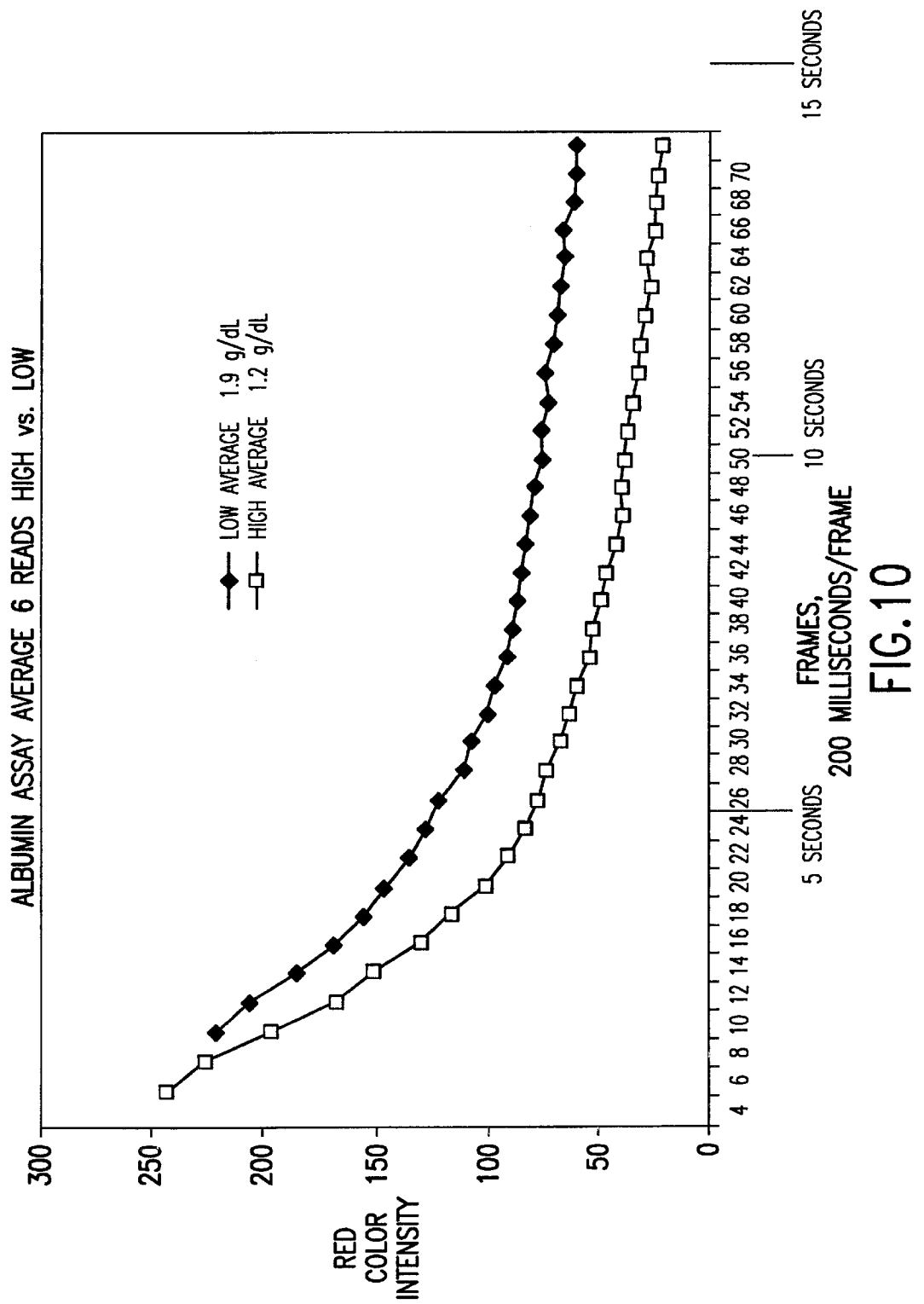
FIG. 10 is a graph of color intensity versus time for the averaged red reflective values of samples having albumin concentrations of 1.2 g/dl and 1.9 g/dl based on an assay run with the present invention and read over 5 seconds.
Figure 11:
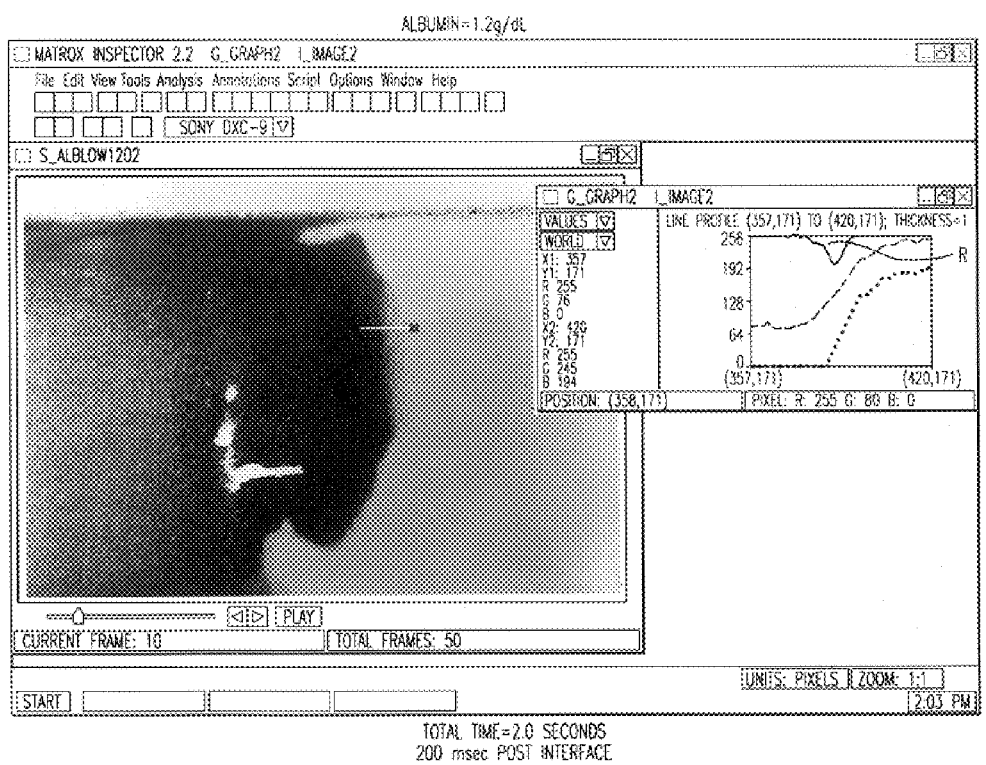
FIG. 11 is a digital color image of an assay run with the present invention of a sample having an albumin concentration of 1.2 g/dl within 200 mseconds of interface formation and 2.0 seconds after sample application, as well as the associated color absorption graph for a selected portion of the digital color image.
Figure 12:
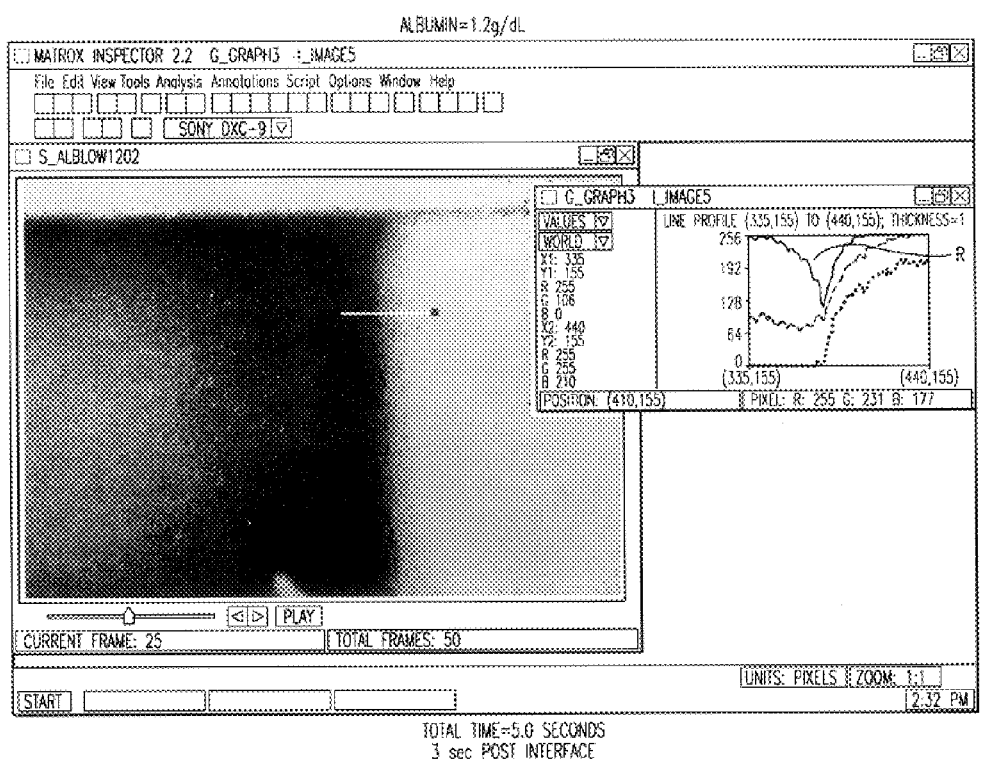
FIG. 12 is a digital color image of an assay run with the present invention of a sample having an albumin concentration of 1.2 g/dl at three (3) seconds after interface formation and five (5) seconds after sample application, as well as the associated color absorption graph for a selected portion of the digital color image.
Figure 13:
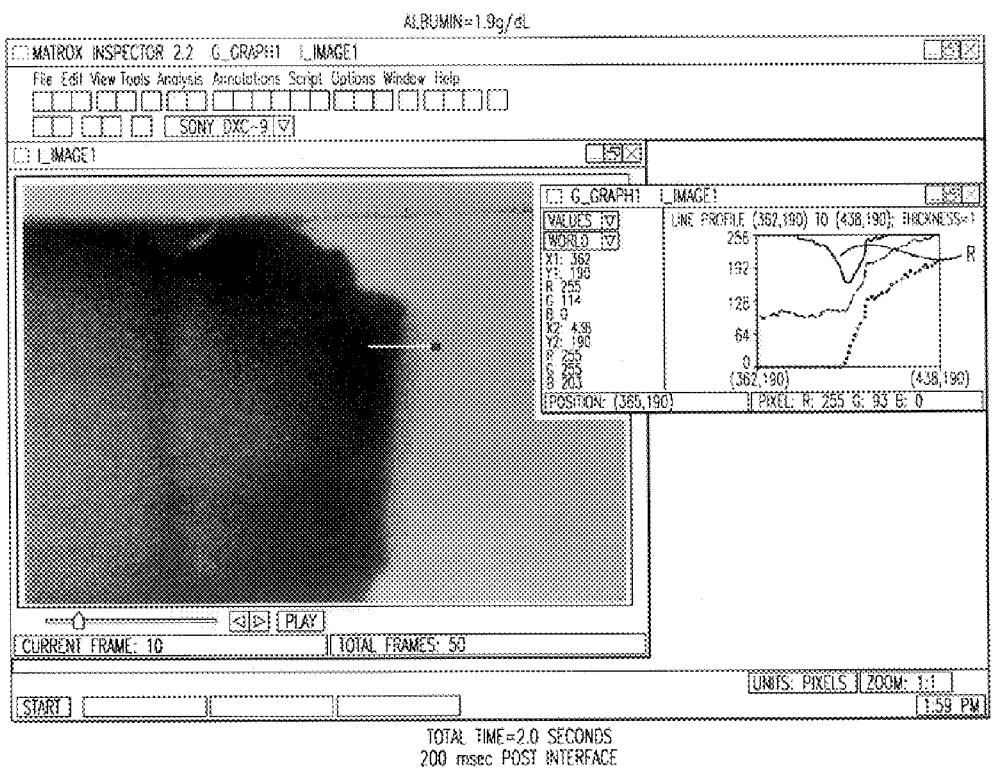
FIG. 13 is a digital color image of an assay run with the present invention of a sample having an albumin concentration of 1.9 g/dl within 200 mseconds of interface formation and 2.0 seconds after sample application, as well as the associated color absorption graph for a selected portion of the digital color image.
Figure 14:
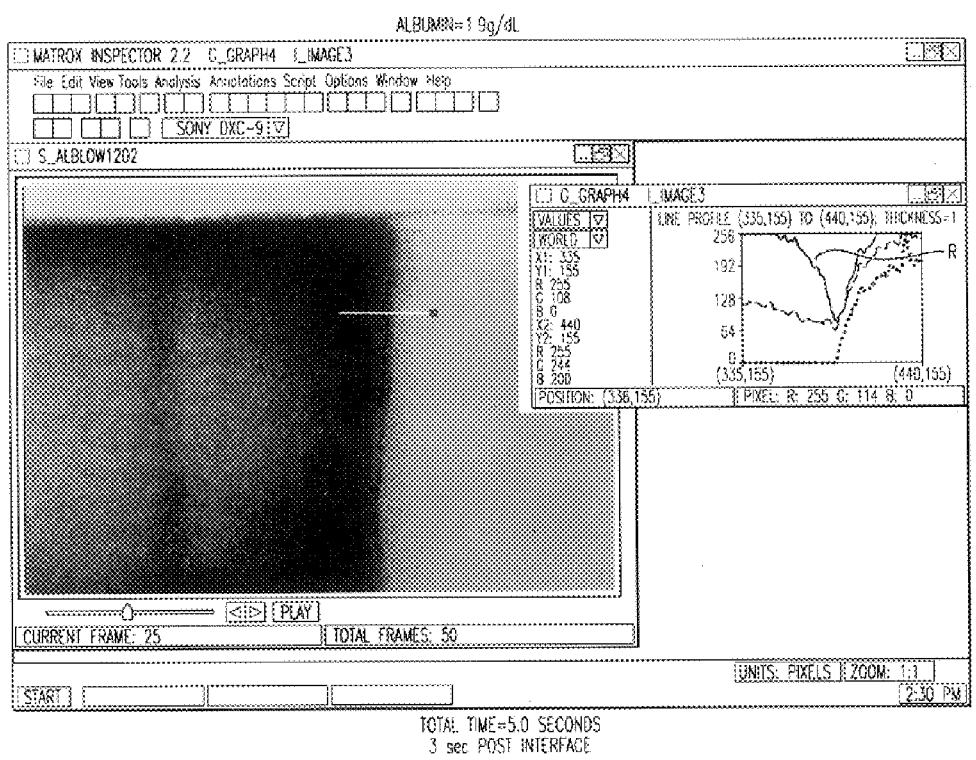
FIG. 14 is a digital color image of an assay run with the present invention of a sample having an albumin concentration of 1.9 g/dl at three (3) seconds after interface formation and five (5) seconds after sample application, as well as the associated color absorption graph for a selected portion of the digital color image.
Figure 15:
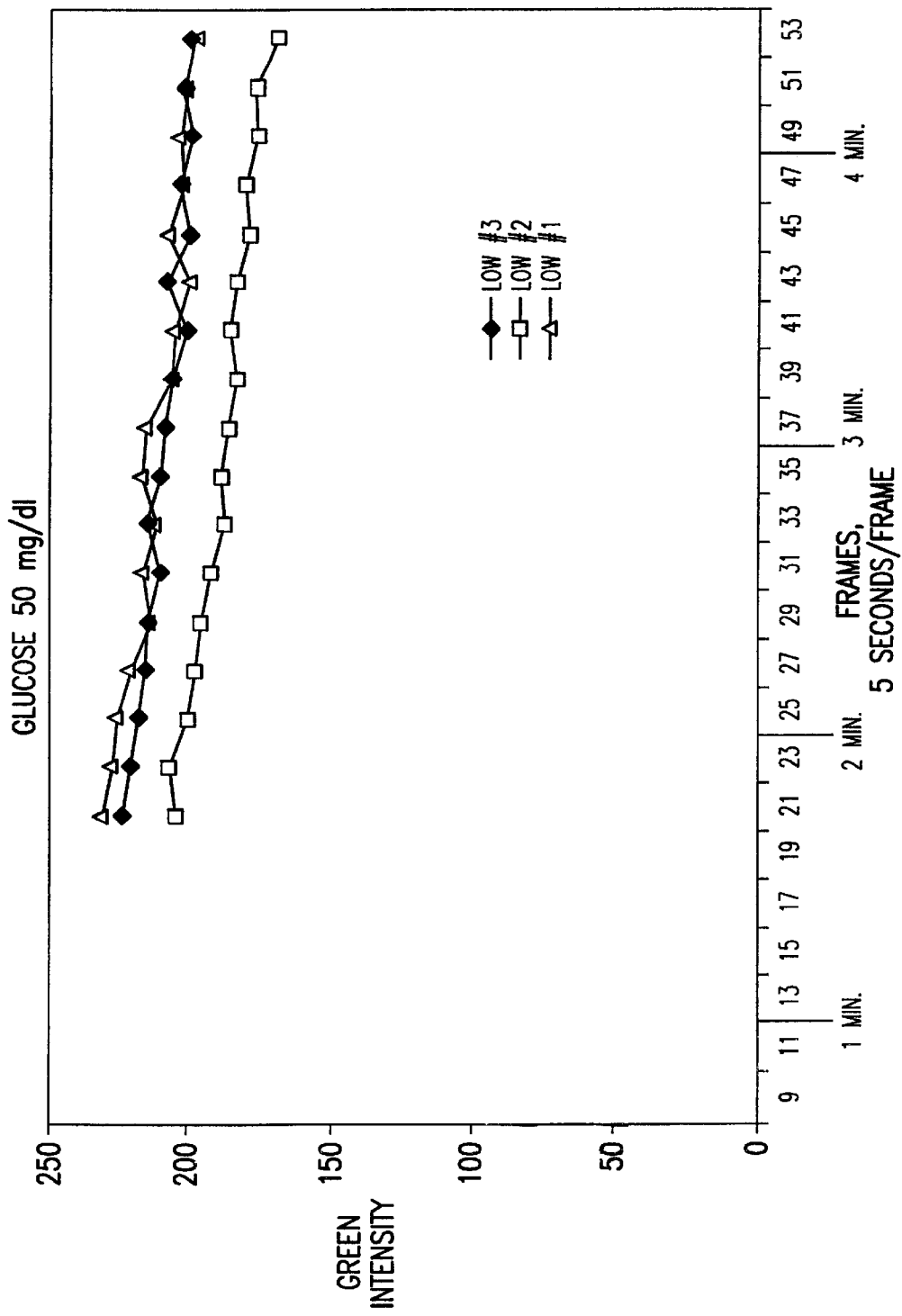
FIG. 15 is a graph of color intensity versus time for three different devices reading a sample having a glucose concentration of 50 mg/dl based on an assay run with the present invention.
Figure 16:
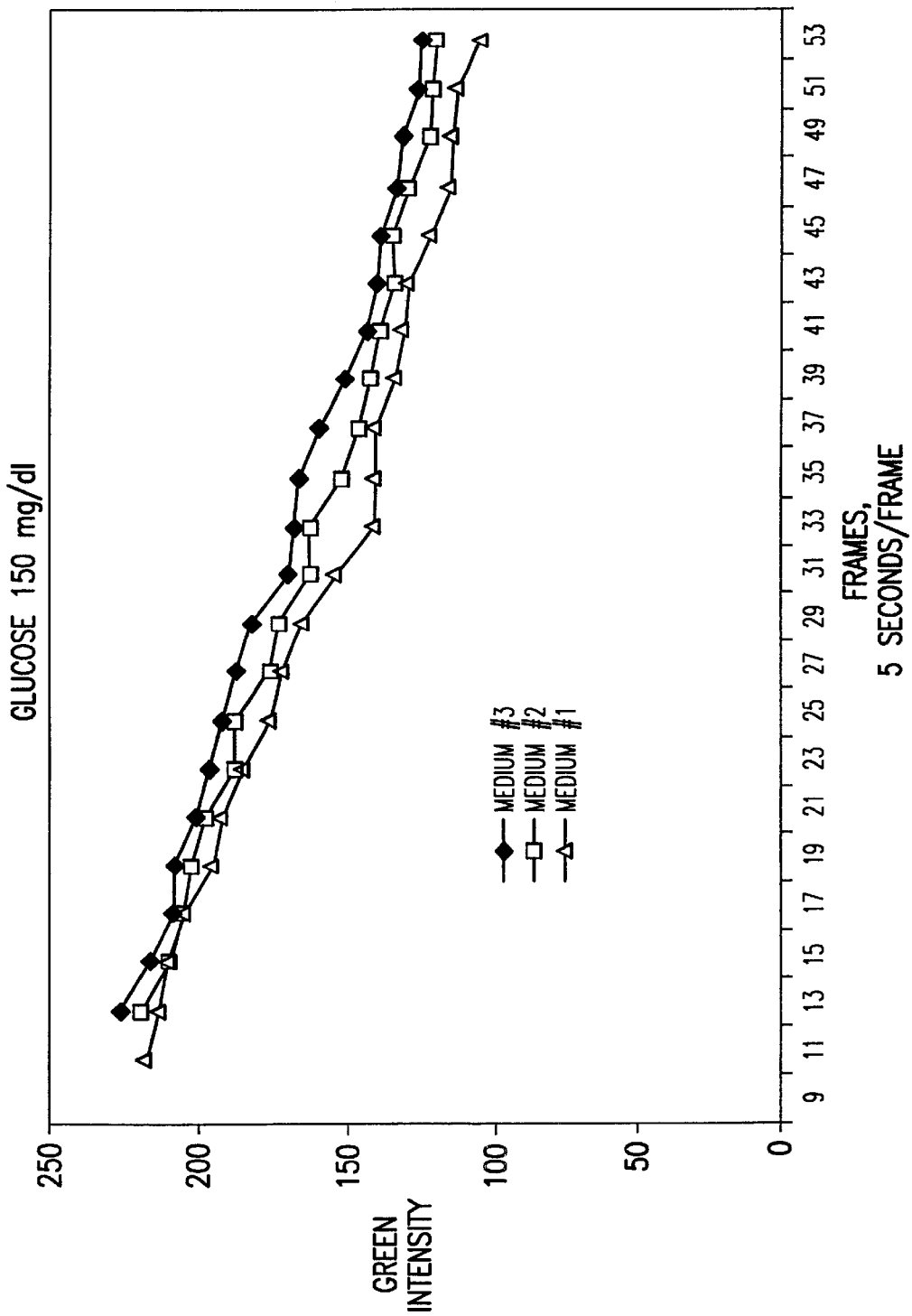
FIG. 16 is a graph of color intensity versus time for three different devices reading a sample having a glucose concentration of 150 mg/dl based on an assay run with the present invention.
Figure 17:
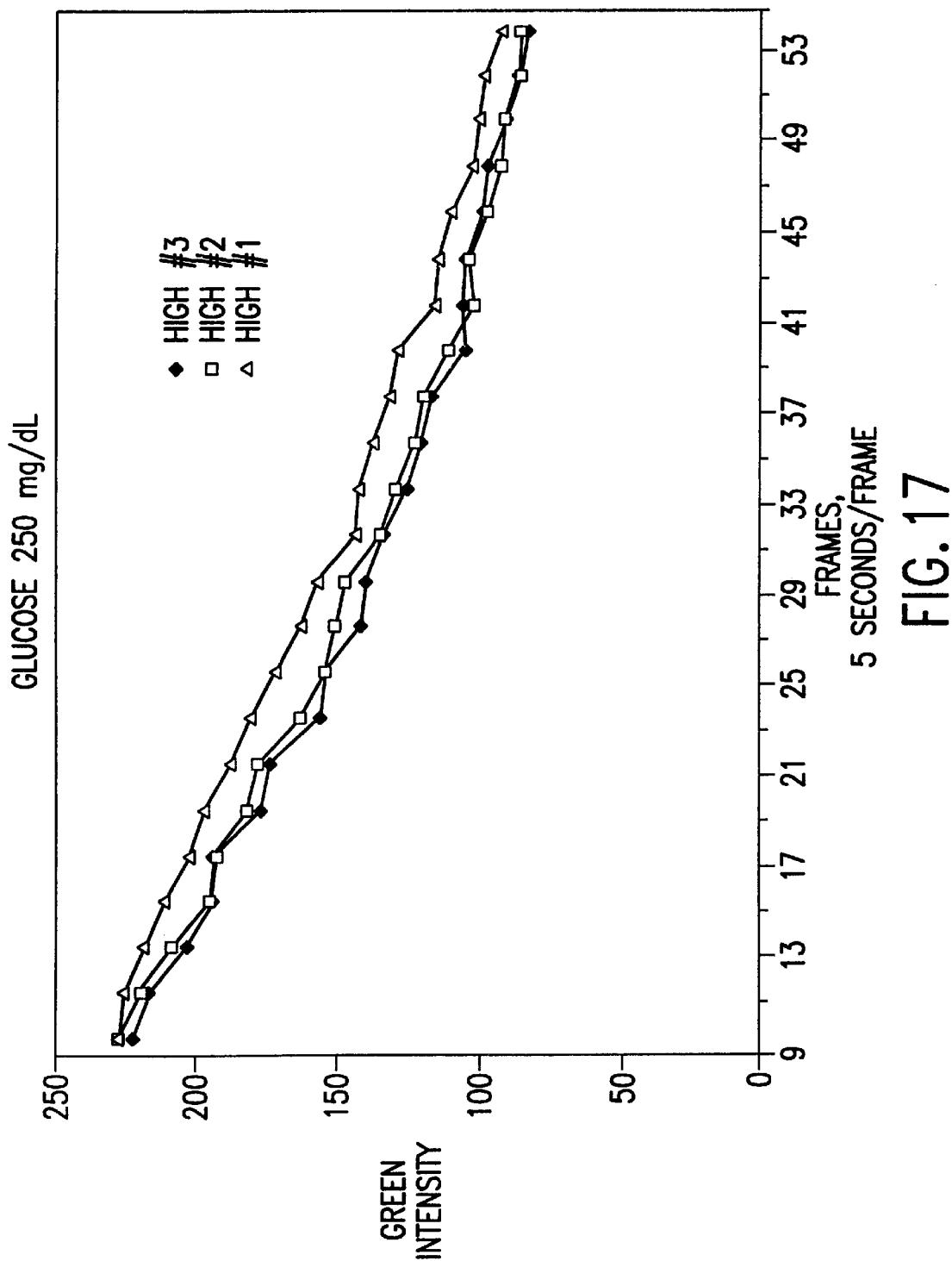
FIG. 17 is a graph of color intensity versus time for three different devices reading a sample having a glucose concentration of 250 mg/dl based on an assay run with the present invention.
Figure 18:
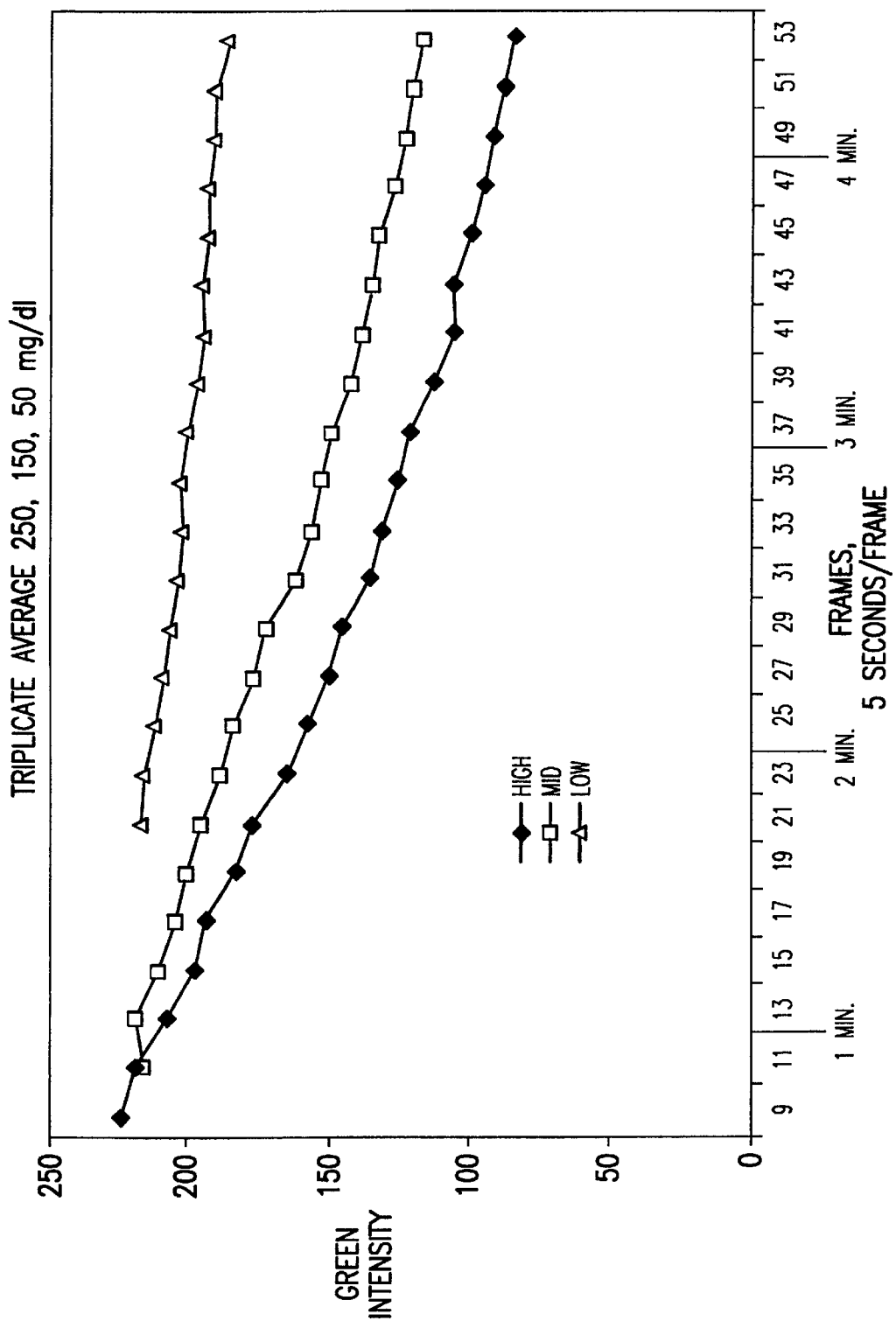
FIG. 18 is a graph of color intensity versus time for the average value of samples having a glucose concentration of 50 mg/dl, 150 mg/dl and 250 mg/dl based on an assay run with the present invention and read over 4.5 minutes.

FIG. 5, 7 and 10 are graphical representations, and FIGS. 5 and 9 are numerical representations, of the color intensity of the reaction product versus time for both of the 1.2 g/dl and 1.9 g/dl samples. These graphs show that the assay performed in accordance with the subject invention produces a substantial color intensity within five (5) seconds from application of the sample to the test strip of the present invention which is proportional to the original analyte concentration based on slope and final color intensity.

FIGS. 11 through 14 are digital photographs of the 1.2 g/dl and 1.9 g/dl test strips at 200 mseconds (2.0 seconds after sample application to the test strip) and at 3.0 seconds after interface formation (5.0 seconds after sample application to the test strip). These digital images were recorded with a Sony Progressive 3CCD camera and the digital data was loaded to a Gateway PC, where a selected line of the images was analyzed using the INSPECTOR color absorption software by Matrox. Comparing FIG. 11 with FIG. 12 for the 1.2 g/dl sample and FIG. 13 with FIG. 14 for the 1.9 g/dl sample, a large increase in red absorption occurred in under three (3) seconds, as shown by line "R" in FIGS. 11 through 14. Thus, the test protocol of the present invention produces an ascertainable reaction at a reaction rate such that the test can be performed in five (5) seconds from sample addition and in three (3) seconds after interface formation.

EXAMPLE 4

This is another example using the protocol of Example 1, and illustrating how a device of the present invention was used to determine the presence and concentration of glucose in a sample of whole blood. In this example, 50 mg/dl, 150 mg/dl and 250 mg/dl samples were used.

A HEMOSEP L® membrane was affixed to an adhesive plastic backing and cut into 4 mm×25 mm strips. 15 µl Trinder reagent (Sigma Chemical Co., St. Louis, Mo.) containing glucose oxidase (15,000 u/L), 4-aminoantypyrine (0.5 mM), p-hydroxybenzene sulfonate (20 mM) and peroxidase (10,000 u/L) at pH approximately 7.0 was added to one end of each test strip, comprising about one-half of the total strip area.

15 µl of serum was added simultaneously to the outer end of the fluid sample side of the strip at the fluid sample application site. The two liquids flowed towards each other, eventually yielding three distinct bands on the strip: a serum band, a red/brown quinoneimine dye reaction product band (the reaction interface), and a band of unreacted Trinder reagent. FIGS. 15 through 18 show the rate of development of the quinoneimine dye product. These graphs show that the assay performed in accordance with the subject invention produces a substantial color intensity within 2–4 minutes from application of the sample to the test strip of the present invention.

EXAMPLE 5

This is another example using the protocol of Example 2, and illustrating how the present invention was applied to detect and quantify calcium in fetal calf serum. In this example, 9.3 mg/dl and 13 mg/dl samples were used.

Figure 19:
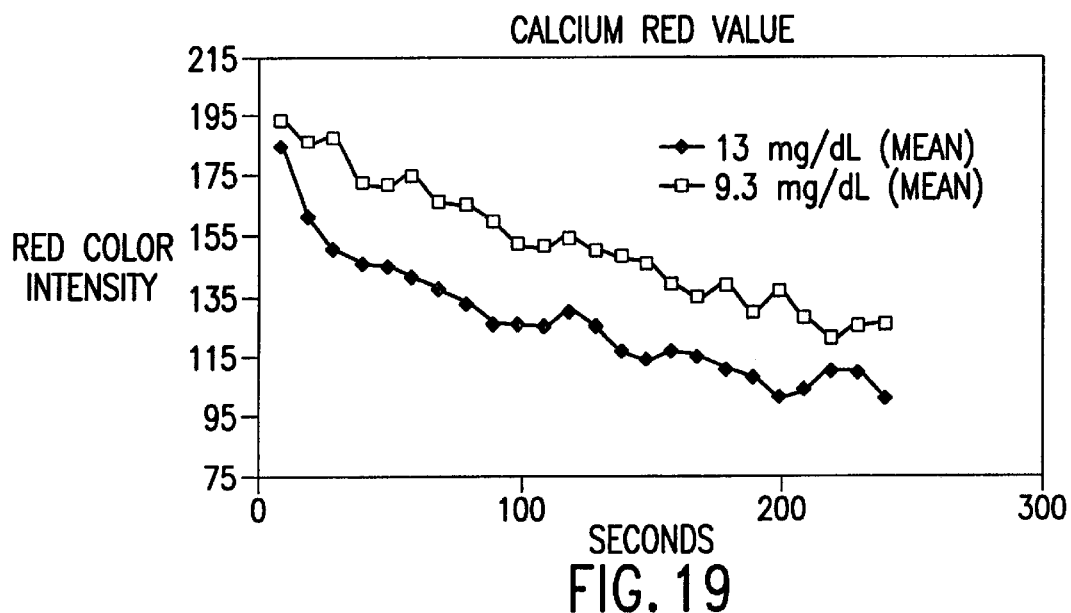
FIG. 19 is a graph of color intensity versus time for samples having calcium concentrations of 9.3 mg/dl and 13 mg/dl based on an assay run with the present invention.
Figure 20:
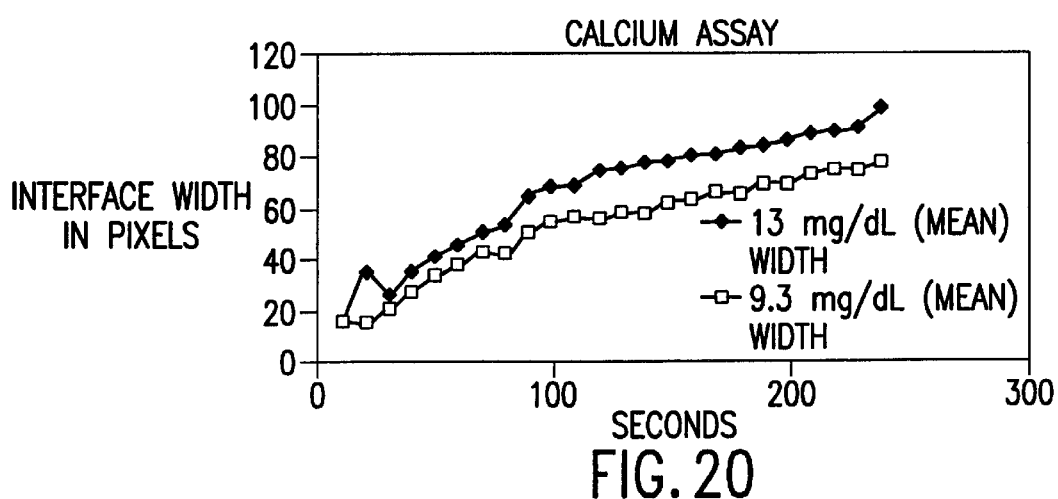
FIG. 20 is a graph of interface width versus time for samples having calcium concentrations of 9.3 mg/dl and 13 mg/dl based on an assay run with the present invention.

Polyethersulfone membranes were prepared as described in Example 1 and washed with 50 µl of water at pH 2.0. Fifteen microliters of fetal calf serum containing 9.3 mg/dl and 13 mg/dl of calcium was added to the fluid sample side of each strip at the fluid sample application site while simultaneously adding 15 µl of acidified Arsenazo III red/purple dye solution to the diluent solution side of the strip at the diluent solution application site. In each case, the two liquids flowed towards each other and upon meeting formed a discrete interface. The blue reaction product, calcium-arsenazo III, developed at the interface. Referring to FIGS. 19 and 20, which show graphical and numerical representations of this example, FIG. 19 shows that the assay performed in accordance with the subject invention produces a substantial color intensity within one minute from application of the sample to the test strip of the present invention.

FIG. 20 shows the relative stability of the interface width over time. The interface width approximately doubles from 100 seconds to 250+ seconds.

What is claimed is:

1. A device for detecting and quantifying at least one analyte in a fluid sample by employing a liquid reactant that reacts with the analyte to form a detectable reaction product, by relating the analyte to the detectable reaction product of analyte and liquid reactant comprising:

a bibulous material having a first zone for the application of the fluid sample suspected of containing analyte, wherein when the fluid sample is added to the first zone, the fluid sample flows in a first direction, and a second zone for the application of the liquid reactant comprising a reagent that reacts with analyte present in the fluid sample to form a detectable product, wherein when the liquid reactant is added to the second zone, the liquid reactant flows in a second direction opposite and toward the first direction;

whereby when the flowing fluid sample and the flowing liquid reactant meet, flow stops and a stable interface is formed at a juncture between and distinct from the fluid sample and the liquid reactant, and whereby the detectable reaction product is formed at the stable interface and has desired wavelengths of reflectance or absorption and is proportional to analyte concentration based on peak intensity of reflectance or absorption of the detectable reaction product.

2. The device of claim 1 wherein the bibulous material is capable of separating red blood cells from the whole blood.

3. The device of claim 1 wherein the bibulous material is nitrocellulose.

4. The device of claim 1 wherein the bibulous material supports the capillary flow of liquids.

5. The device of claim 1 wherein the detectable reaction product reflects light.

6. A device for detecting and quantifying at least one analyte in a fluid sample by employing a liquid reactant that reacts with the analyte to form a detectable reaction product, by relating the analyte to the detectable reaction product of analyte and liquid reactant comprising:

a bibulous material having a first zone for the application of the fluid sample suspected of containing analyte, wherein when the fluid sample is added to the first zone, the fluid sample flows in a first direction, and a second zone for the application of the liquid reactant comprising a reagent that reacts with analyte present in the fluid sample to form a detectable product, wherein when the liquid reactant is added to the second zone, the liquid reactant flows in a second direction opposite and toward the first direction;

whereby when the flowing fluid sample and the flowing liquid reactant meet, flow stops and a stable interface is formed at a juncture between and distinct from the fluid sample and the liquid reactant, and whereby the detectable reaction product forms at a rate sufficient for it to be detected within about fifteen seconds after application of the fluid sample to the fluid sample zone.

7. The device of claim 6 wherein the bibulous material is capable of separating red blood sales from whole blood.

8. The device of claim 6 wherein the bibulous material is nitrocellulose.

9. The device of claim 6 wherein the bibulous material supports the capillary flow of liquids.

10. The device of claim 6 wherein the detectable reaction products reflects light.

11. A device for detecting and quantifying at least one analyte in a fluid sample by employing a liquid reactant that reacts with the analyte to form a detectable reaction product, by relating the analyte to the detectable product of analyte and liquid reactant comprising:

bibulous material having a first zone for the application of the fluid sample suspected of containing analyte, wherein when the fluid sample is added to the first zone, the fluid sample flows in a first direction, and a second zone for the application of a liquid adjacent to a reconstitutable reagent located on the bibulous material, the reagent and the liquid forming the liquid reactant that reacts with analyte present in the fluid sample to form a detectable product, wherein when the liquid reactant is present is the second zone, the liquid reactant flows in a second direction opposite and toward the first direction:

whereby when the flowing fluid sample and the flowing liquid reactant meet, flow stops and a stable interface is formed at a juncture between and distinct from the fluid sample and the liquid reactant, and whereby the detectable reaction product has desired wavelengths of reflectance or absorption and is proportional to analyte concentration based on peak intensity of reflectance or absorption of the detectable reaction product.

12. The device of claim 11 wherein the bibulous material is capable of separating red blood cells from whole blood.

13. The device of claim 11 wherein the bibulous material is nitrocellulose.

14. The device of claim 11 wherein the bibulous material supports the capillary flow of liquids.

15. The device of claim 11, wherein the detectable reaction product reflects light.

16. A device for detecting and quantifying at least one analyte in a fluid sample by employing a liquid reactant that reacts with the analyte to form a detectable reaction product, by relating the analyte to the detectable reaction product of analyte and liquid reactant comprising:

a bibulous material having a first zone for the application of the fluid sample suspected of containing analyte, wherein when the fluid sample is added to the first zone, and the fluid sample flows in a first direction, and a second zone for the application of the liquid reactant comprising a reagent that reacts with analyte present in the fluid sample to form a detectable product, wherein when the liquid reactant is added to the second zone, the liquid reactant flows in a second direction opposite and toward the first direction;

whereby when the flowing fluid sample and the flowing liquid reactant meet, flow stops and a stable interface is formed at a juncture between and distinct from the fluid sample and the liquid reactant, and whereby the detectable reaction product has desired wavelengths of reflectance or absorption and the detectable reaction product is formed at a rate proportional to concentration of the analyte.

17. The device of claim 16, wherein the bibulous material is capable of separating red blood cells from the whole blood.

18. The device of claim 16, wherein the bibulous material is nitrocellulose.

19. The device of claim 16 wherein the bibulous material supports the capillary flow of liquids.

20. The device of claim 16, wherein the detectable reaction product reflects light.

21. A device for detecting and quantifying at least one analyte in a fluid sample by employing a liquid reactant that reacts with the analyte to form a detectable reaction product, by relating the analyte to the detectable reaction product of analyte and liquid reactant comprising:

a bibulous material having a first zone for the application of the fluid sample suspected of containing analyte, wherein when the fluid sample is added to the first zone the fluid sample flows in a first direction, and a second zone for the application of the liquid reactant comprising a reagent that reacts with analyte present in the fluid sample to form a detectable product, wherein when the liquid reactant is added to the second zone, the liquid reactant flows in a second direction opposite and toward the first direction;

whereby when the flowing fluid sample and flowing liquid reactant meet, flow stops and a stable interface is formed at a juncture between and distinct from the fluid sample and the liquid reactant, and whereby the detectable reaction product has desired wavelengths of reflectance or absorption and the detectable reaction product may be formed in an amount sufficient to cause a predetermined threshold intensity of reflectance or absorption indicative of the presence of the analyte.

22. The device of claim 21 wherein the bibulous material is capable of separating red blood cells from the whole blood.

23. The device of claim 21 wherein the bibulous material is nitrocellulose.

24. The device of claim 21 wherein the bibulous material supports the capillary flow of liquids.

25. The device of claim 21 wherein the detectable reaction product reflects light.

26. A device for detecting and quantifying at least one analyte in a fluid sample by employing a liquid reactant that reacts with the analyte to form a detectable reaction product, by relating the analyte to the detectable reaction product of analyte and liquid reactant comprising:

a bibulous material having a first zone for the application of the fluid sample suspected of containing analyte, wherein when the fluid sample is added to the first zone, the fluid sample flows in a first direction, and a second zone for the application of the liquid reactant comprising a reagent that reacts with analyte present in the fluid sample to form a detectable product, wherein when the liquid reactant is added to the second zone, the liquid reactant flows in a second direction opposite and toward the first direction;

whereby when the flowing fluid sample and the flowing liquid reactant meet, flow stops and a stable interface is formed at a juncture between and distinct from the fluid sample and the liquid reactant, and whereby the detectable reaction product has desired wavelengths of reflectance or absorption from about 250 nanometers to about 700 nanometers and is proportional to analyte concentration based on peak intensity of reflectance or absorption of the detectable reaction product.

27. The device of claim 26 wherein the bibulous material is capable of separating red blood cells from the whole blood.

28. The device of claim 26 wherein the bibulous material is nitrocellulose.

29. The device of claim 26 wherein the bibulous material supports the capillary flow of liquids.

30. The device of claim 26, wherein the detectable reaction product reflects light.

* * * * *